US010858627B2

(12) United States Patent
Garry et al.

(10) Patent No.: US 10,858,627 B2
(45) Date of Patent: Dec. 8, 2020

(54) REGULATION OF MESODERMAL SPECIFICATION

(71) Applicant: Regents of the University of Minnesota, Minneapolis, MN (US)

(72) Inventors: Daniel J. Garry, Eagan, MN (US); Naoko Koyano-Nakagawa, Shoreview, MN (US); Mary G. Garry, Eagan, MN (US); Bhairab Singh, Falcon Heights, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/748,772

(22) PCT Filed: Jul. 29, 2016

(86) PCT No.: PCT/US2016/044859
§ 371 (c)(1),
(2) Date: Jan. 30, 2018

(87) PCT Pub. No.: WO2017/020009
PCT Pub. Date: Feb. 2, 2017

(65) Prior Publication Data
US 2019/0010458 A1    Jan. 10, 2019

Related U.S. Application Data

(60) Provisional application No. 62/199,044, filed on Jul. 30, 2015.

(51) Int. Cl.
*C12N 5/0789* (2010.01)
*A61K 35/44* (2015.01)
*C12N 5/0735* (2010.01)
*A01K 67/027* (2006.01)
*A61K 48/00* (2006.01)
*A61P 9/00* (2006.01)
*A61P 17/02* (2006.01)
*C12N 5/071* (2010.01)
*C12N 5/074* (2010.01)
*C12N 5/00* (2006.01)

(52) U.S. Cl.
CPC ........ *C12N 5/0647* (2013.01); *A01K 67/0276* (2013.01); *A61K 48/00* (2013.01); *A61P 9/00* (2018.01); *A61P 17/02* (2018.01); *C12N 5/0606* (2013.01); *C12N 5/0692* (2013.01); *C12N 5/0696* (2013.01); *A61K 35/44* (2013.01); *C12N 5/0018* (2013.01); *C12N 2310/141* (2013.01); *C12N 2501/65* (2013.01); *C12N 2506/02* (2013.01); *C12N 2506/45* (2013.01)

(58) Field of Classification Search
CPC .. C12N 5/0647; C12N 5/0692; C12N 5/0696; C12N 5/0606; C12N 2501/65; C12N 5/0018; C12N 2310/141; C12N 2506/02; C12N 2506/45; A01K 67/0276; A61K 48/00; A61K 35/44; A61P 9/00; A61P 17/02
See application file for complete search history.

(56) References Cited

U.S. PATENT DOCUMENTS

| 2008/0025955 | A1* | 1/2008 | Nakao .................... C12N 5/069 424/93.7 |
| 2009/0176723 | A1 | 7/2009 | Brown et al. |
| 2010/0184032 | A1 | 7/2010 | Georgantas et al. |
| 2012/0135051 | A1 | 5/2012 | Chien et al. |

FOREIGN PATENT DOCUMENTS

WO    WO-2017020009 A1    2/2017

OTHER PUBLICATIONS

Ren et al. MicroRNA and gene expression patterns in the differentiation of human embryonic stem cells. Journal of Translational Medicine 2009, 7:20. p. 1-17 (Year: 2009).*
Singh et al. Etv2/mir-130a/pdgfra Pathway Regulates Endothelial Lineage Specification. Abstract 19652. Circulation. Originally published Nov. 25, 2014. p. 1-5. (Year: 2014).*
"International Application Serial No. PCT US2016 044859, International Preliminary Report on Patentability dated Feb. 8, 2018", 10 pgs.
"International Application Serial No. PCT/US2016/044859; International Search Report dated Dec. 1, 2016", 7 pgs.
"International Application Serial No. PCT/US2016/044859; Invitation to Pay Add'l Fees and Partial Search Report dated Sep. 20, 2016", 2 pgs.
"International Application Serial No. PCT/US2016/044859, Written Opinion dated Dec. 1, 2016", 8 pgs.
Kataoka, et al., "Etv2/ER71 induces vascular mesoderm from Flk1 PDGFR primitive mesoderm Blood", vol. 118(26),col. 1, para 1; p. 6978, col. 2. para1; and p. 6984, Fig 7C, (2011), 6975-86.
Marcola, "Endothelial Progenitor Cells in Tumor Angiogenesis: Another Brick in the Wall. Stem Cells Int", 2015:832649. Epub Apr. 27, 2015. PDF File: p. 1-10. Abstract;p. 2, col. 1; p. 3, Fig 1, and p. 6, Fig 2, (2015), 1-10.

(Continued)

*Primary Examiner* — Taeyoon Kim
(74) *Attorney, Agent, or Firm* — Schwegman Lundberg & Woessner, P.A.

(57) ABSTRACT

Disclosed is a method to differentiate stem, progenitor or precursor cells comprising contacting said stem, progenitor or precursor cells with miR-130a, or an RNA having at least 95% identity thereto, so as to yield cells of endothelial lineage. Further disclosed are compositions comprising the endothelial lineage cells obtained and methods of using the compositions for treating diseases including cardiovascular diseases.

6 Claims, 9 Drawing Sheets
Specification includes a Sequence Listing.

(56) References Cited

OTHER PUBLICATIONS

Meng, et al., "Downregulation of MicroRNA-130a Contributes to Endothelial Progenitor Cell Dysfunction in Diabetic Patients via Its Target Runx3", (2013), 1-10 pgs.

Rusu, et al., "G protein-dependent basal and evoked endothelial cell vWF secretion", (2014), 442-450.

Singh, et al., "Etv2-miR-130a network regulates mesodermal specification", vol. 13(5), p. 915-23. Epub Oct. 22, 2015. PDF File Entire documentation, especially Abstract, (Nov. 2015).

* cited by examiner

Graphical Abstract

SEQUENCE LISTING

```
<160> NUMBER OF SEQ ID NOS: 25

<210> SEQ ID NO 1
<211> LENGTH: 64
<212> TYPE: RNA
<213> ORGANISM: Mus musculus

<400> SEQUENCE: 1
gagcucuuuu cacauugugc uacugucuaa cguguaccga gcagugcaau guuaaagggg     60
cauc                                                                 64

<210> SEQ ID NO 2
<211> LENGTH: 82
```

```
<212> TYPE: RNA
<213> ORGANISM: Mus musculus

<400> SEQUENCE: 2
ggcuuguugg acacucuuuc ccuguugcac uacuguggge cucugggaag cagugcaaug      60
augaaagggc aucugucggg cc                                              82

<210> SEQ ID NO 3
<211> LENGTH: 89
<212> TYPE: RNA
<213> ORGANISM: Homo sapiens

<400> SEQUENCE: 3
ugcugcuggc cagagcucuu uucacauugu gcuacugucu gcaccuguca cuagcagugc      60
aauguuaaaa gggcauuggc cguguagug                                       89

<210> SEQ ID NO 4
<211> LENGTH: 82
<212> TYPE: RNA
<213> ORGANISM: Homo sapiens

<400> SEQUENCE: 4
ggccugcccg acacucuuuc ccuguugcac uacuauaggc cgcugggaag cagugcaaug      60
augaaagggc aucggucagg uc                                              82

<210> SEQ ID NO 5
<211> LENGTH: 22
<212> TYPE: RNA
<213> ORGANISM: Homo sapiens

<400> SEQUENCE: 5
cagugcaaug uuaaaagggc au                                              22

<210> SEQ ID NO 6
<211> LENGTH: 26
<212> TYPE: DNA
<213> ORGANISM: Artificial Sequence
<220> FEATURE:
<223> OTHER INFORMATION: A synthetic oligonucleotide

<400> SEQUENCE: 6
gaatataggc aggaaattga ccagat                                          26

<210> SEQ ID NO 7
<211> LENGTH: 26
<212> TYPE: DNA
<213> ORGANISM: Artificial Sequence
<220> FEATURE:
<223> OTHER INFORMATION: A synthetic oligonucleotide

<400> SEQUENCE: 7
atctggtcaa tttcctgcct atattc                                          26

<210> SEQ ID NO 8
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 8
gctttgggtg aggctaaaac g                                               21
```

<210> SEQ ID NO 9
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 9
cagaagccct gttcccagat g                                          21

<210> SEQ ID NO 10
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 10
caatgccctt ttaacattgc actgc                                      25

<210> SEQ ID NO 11
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 11
caataccatt ttaaaattac actac                                      25

<210> SEQ ID NO 12
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 12
caatgccctt ttaacattgc actgc                                      25

<210> SEQ ID NO 13
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 13
caataccatt ttaaaattac actac                                      25

<210> SEQ ID NO 14
<211> LENGTH: 1050
<212> TYPE: DNA
<213> ORGANISM: Mus musculus

<400> SEQUENCE: 14
agaaccgtca gaacaagcat ccatggacct gtggaactgg gatgaggcgt cactgcagga      60
agtgcctcct gggacaagc tgacaggact gggagcggaa tttggtttct atttccctga     120
agtggctcta caagaggaca caccgatcac accaatgaac gtagaaggct gctggaaagg     180
gttcccagag ctggactgga accccgcttt acctcacgaa gacgtacctt tccaggcgga     240
gcccgttgct cacccccttc cgtggtcgcg agactggaca gacctgggat gcaacacctc     300
ggacccgtgg agctgtgctt cacagacgcc aggccctgcc cctcctggca cgagcccctc     360

```
cccttcgtc ggctttgaag gggcgaccgg ccagaatcct gccacctcgg caggaggggt      420
ccctcgtgg tcgcaccctc cagctgcctg gagcactacc agctgggact gttctgtggg      480
cccagtggc gccacctact gggacaatgg cctgggcggg aagcgcatg aggactataa       540
aatgtcatgg ggcgggtctg ccggttcgga ctacaccacc acgtggaata ctgggctgca     600
ggactgcagc atcccttcg aggggcacca gagtccagca ttcaccacgc cctccaaatc     660
gaacaagcag tctgatagag ccacattgac tcgctactcc aaaactaacc accgaggtcc     720
cattcagctg tggcaattcc tcctggagct gctccacgac ggggctcgca gcagctgcat     780
ccgctggacg ggcaatagcc gcgagttcca gctgtgcgac cccaaagagg tggcccggct     840
gtggggcgag cgcaagagga agccgggaat gaattatgag aaactgagtc gaggtctacg     900
ttattattac cgccgcgaca tcgtgctcaa gagtggtggg cgcaagtaca cataccgctt     960
cgggggacgt gtgcctgtcc tcgcctatca ggatgatatg gggcatctgc caggtgcaga    1020
aggccaataa acaaaaaaac aaaaacaaaa                                     1050
```

<210> SEQ ID NO 15
<211> LENGTH: 335
<212> TYPE: PRT
<213> ORGANISM: Mus musculus

<400> SEQUENCE: 15

```
Met Asp Leu Trp Asn Trp Asp Glu Ala Ser Leu Gln Glu Val Pro Pro
1               5                   10                  15
Gly Asp Lys Leu Thr Gly Leu Gly Ala Glu Phe Gly Phe Tyr Phe Pro
                20                  25                  30
Glu Val Ala Leu Gln Glu Asp Thr Pro Ile Thr Pro Met Asn Val Glu
            35                  40                  45
Gly Cys Trp Lys Gly Phe Pro Glu Leu Asp Trp Asn Pro Ala Leu Pro
        50                  55                  60
His Glu Asp Val Pro Phe Gln Ala Glu Pro Val Ala His Pro Leu Pro
65                  70                  75                  80
Trp Ser Arg Asp Trp Thr Asp Leu Gly Cys Asn Thr Ser Asp Pro Trp
                85                  90                  95
Ser Cys Ala Ser Gln Thr Pro Gly Pro Ala Pro Pro Gly Thr Ser Pro
            100                 105                 110
Ser Pro Phe Val Gly Phe Glu Gly Ala Thr Gly Gln Asn Pro Ala Thr
        115                 120                 125
Ser Ala Gly Gly Val Pro Ser Trp Ser His Pro Pro Ala Ala Trp Ser
    130                 135                 140
Thr Thr Ser Trp Asp Cys Ser Val Gly Pro Ser Gly Ala Thr Tyr Trp
145                 150                 155                 160
Asp Asn Gly Leu Gly Gly Glu Ala His Glu Asp Tyr Lys Met Ser Trp
                165                 170                 175
Gly Gly Ser Ala Gly Ser Asp Tyr Thr Thr Thr Trp Asn Thr Gly Leu
            180                 185                 190
Gln Asp Cys Ser Ile Pro Phe Glu Gly His Gln Ser Pro Ala Phe Thr
        195                 200                 205
Thr Pro Ser Lys Ser Asn Lys Gln Ser Asp Arg Ala Thr Leu Thr Arg
    210                 215                 220
Tyr Ser Lys Thr Asn His Arg Gly Pro Ile Gln Leu Trp Gln Phe Leu
225                 230                 235                 240
Leu Glu Leu Leu His Asp Gly Ala Arg Ser Ser Cys Ile Arg Trp Thr
```

```
                245                 250                 255
Gly Asn Ser Arg Glu Phe Gln Leu Cys Asp Pro Lys Glu Val Ala Arg
            260                 265                 270

Leu Trp Gly Glu Arg Lys Arg Lys Pro Gly Met Asn Tyr Glu Lys Leu
        275                 280                 285

Ser Arg Gly Leu Arg Tyr Tyr Tyr Arg Arg Asp Ile Val Leu Lys Ser
    290                 295                 300

Gly Gly Arg Lys Tyr Thr Tyr Arg Phe Gly Arg Val Pro Val Leu
305                 310                 315                 320

Ala Tyr Gln Asp Asp Met Gly His Leu Pro Gly Ala Glu Gly Gln
                325                 330                 335

<210> SEQ ID NO 16
<211> LENGTH: 1510
<212> TYPE: DNA
<213> ORGANISM: Homo sapiens

<400> SEQUENCE: 16
ttcctgttgc agataagccc agcttagccc agctgacccc agaccctctc ccctcactcc      60
ccccatgtcg caggatcgag accctgaggc agacagcccg ttcaccaagc cccccgcccc     120
gcccccatca ccccgtaaac ttctcccagc ctccgccctg ccctcaccca gcccgctgtt     180
ccccaagcct cgctccaagc ccacgccacc cctgcagcag ggcagcccca gaggccagca     240
cctatccccg aggctggggt cgaggctcgg ccccgcccct gcctctgcaa cttgagcctg     300
gctgcgaccc ctgctctgac gtctcggaaa attccccctt gcccaggccc ttggggagg      360 gggtgcatgg tatgaaatgg ggctgagacc cccggctggg ggcagaggaa cccgccagag     420
aacattcaga aggccttcat cgcatccatg gacctgtgga actgggatga ggcatcccca     480
caggaagtgc ctccagggaa caagctggca gggcttgaag gagccaaatt aggcttctgt     540
ttccctgatc tggcactcca aggggacacg ccgacagcga cagcagagac atgctggaaa     600
ggtacaagct catccctggc aagcttccca cagctggact ggggctccgc gttactgcac     660
ccagaagttc catgggggc ggagcccgac tctcaggctc ttccgtggtc cggggactgg      720
acagacatgg cgtgcacagc ctgggactct tggagcggcg cctcgcagac cctgggcccc     780
gcccctctcg gcccgggccc catccccgcc gccggctccg aaggcgccgc gggccagaac     840
tgcgtccccg tggcgggaga ggccacctcg tggtcgcgcg cccaggccgc cgggagcaac     900
accagctggg actgttctgt ggggcccgac ggcgatacct actggggcag tggcctgggc     960
ggggagccgc gcacggactg taccatttcg tggggcgggc ccgcgggccc ggactgtacc    1020
acctcctgga acccgggct gcatgcgggt ggcaccacct ctttgaagcg gtaccagagc    1080
tcagctctca ccgtttgctc cgaaccgagc ccgcagtcgg accgtgccag tttggctcga    1140
tgccccaaaa ctaaccaccg aggtcccatt cagctgtggc agttcctcct ggagctgctc    1200
cacgacgggg cgcgtagcag ctgcatccgt tggactggca acagccgcga gttccagctg    1260
tgcgacccca agaggtggcc tcggctgtgg ggcgagcgca agagaaagcc gggcatgaat    1320
tacgagaagc tgagccgggg ccttcgctac tactatcgcc gcgacatcgt gcgcaagagc    1380
ggggggcgaa agtacacgta ccgcttcggg ggccgcgtgc ccagcctagc ctatccggac    1440
tgtgcgggag gcggacgggg agcagagaca caataaaaat tcccggtcaa acctcaaaaa    1500
aaaaaaaaaa                                                           1510

<210> SEQ ID NO 17
```

<211> LENGTH: 342
<212> TYPE: PRT
<213> ORGANISM: Homo sapiens

<400> SEQUENCE: 17

```
Met Asp Leu Trp Asn Trp Asp Glu Ala Ser Pro Gln Glu Val Pro Pro
1               5                   10                  15

Gly Asn Lys Leu Ala Gly Leu Glu Gly Ala Lys Leu Gly Phe Cys Phe
            20                  25                  30

Pro Asp Leu Ala Leu Gln Gly Asp Thr Pro Thr Ala Thr Ala Glu Thr
        35                  40                  45

Cys Trp Lys Gly Thr Ser Ser Ser Leu Ala Ser Phe Pro Gln Leu Asp
50                  55                  60

Trp Gly Ser Ala Leu Leu His Pro Glu Val Pro Trp Gly Ala Glu Pro
65                  70                  75                  80

Asp Ser Gln Ala Leu Pro Trp Ser Gly Asp Trp Asp Met Ala Cys
                85                  90                  95

Thr Ala Trp Asp Ser Trp Ser Gly Ala Ser Gln Thr Leu Gly Pro Ala
            100                 105                 110

Pro Leu Gly Pro Gly Pro Ile Pro Ala Ala Gly Ser Glu Gly Ala Ala
        115                 120                 125

Gly Gln Asn Cys Val Pro Val Ala Gly Glu Ala Thr Ser Trp Ser Arg
130                 135                 140

Ala Gln Ala Ala Gly Ser Asn Thr Ser Trp Asp Cys Ser Val Gly Pro
145                 150                 155                 160

Asp Gly Asp Thr Tyr Trp Gly Ser Gly Leu Gly Gly Glu Pro Arg Thr
                165                 170                 175

Asp Cys Thr Ile Ser Trp Gly Gly Pro Ala Gly Pro Asp Cys Thr Thr
            180                 185                 190

Ser Trp Asn Pro Gly Leu His Ala Gly Gly Thr Thr Ser Leu Lys Arg
        195                 200                 205

Tyr Gln Ser Ser Ala Leu Thr Val Cys Ser Glu Pro Ser Pro Gln Ser
210                 215                 220

Asp Arg Ala Ser Leu Ala Arg Cys Pro Lys Thr Asn His Arg Gly Pro
225                 230                 235                 240

Ile Gln Leu Trp Gln Phe Leu Leu Glu Leu Leu His Asp Gly Ala Arg
                245                 250                 255

Ser Ser Cys Ile Arg Trp Thr Gly Asn Ser Arg Glu Phe Gln Leu Cys
            260                 265                 270

Asp Pro Lys Glu Val Ala Arg Leu Trp Gly Glu Arg Lys Arg Lys Pro
        275                 280                 285

Gly Met Asn Tyr Glu Lys Leu Ser Arg Gly Leu Arg Tyr Tyr Tyr Arg
290                 295                 300

Arg Asp Ile Val Arg Lys Ser Gly Gly Arg Lys Tyr Thr Tyr Arg Phe
305                 310                 315                 320

Gly Gly Arg Val Pro Ser Leu Ala Tyr Pro Asp Cys Ala Gly Gly Gly
                325                 330                 335

Arg Gly Ala Glu Thr Gln
            340
```

<210> SEQ ID NO 18
<211> LENGTH: 14
<212> TYPE: RNA
<213> ORGANISM: Danio rerio

<400> SEQUENCE: 18

```
auuuucacuu auca                                                      14

<210> SEQ ID NO 19
<211> LENGTH: 15
<212> TYPE: RNA
<213> ORGANISM: Xenopus laevis

<400> SEQUENCE: 19
auuuucacgu uguca                                                     15

<210> SEQ ID NO 20
<211> LENGTH: 15
<212> TYPE: RNA
<213> ORGANISM: Mus musculus

<400> SEQUENCE: 20
guuuucacgu uguca                                                     15

<210> SEQ ID NO 21
<211> LENGTH: 15
<212> TYPE: RNA
<213> ORGANISM: Homo sapiens

<400> SEQUENCE: 21
guuuucacgu uguca                                                     15

<210> SEQ ID NO 22
<211> LENGTH: 15
<212> TYPE: RNA
<213> ORGANISM: Homo sapiens

<400> SEQUENCE: 22
uagcagugca auguu                                                     15

<210> SEQ ID NO 23
<211> LENGTH: 15
<212> TYPE: RNA
<213> ORGANISM: Mus musculus

<400> SEQUENCE: 23
gagcagugca auguu                                                     15

<210> SEQ ID NO 24
<211> LENGTH: 15
<212> TYPE: RNA
<213> ORGANISM: Xenopus laevis

<400> SEQUENCE: 24
aagcagugca auguu                                                     15

<210> SEQ ID NO 25
<211> LENGTH: 15
<212> TYPE: RNA
<213> ORGANISM: Danio rerio

<400> SEQUENCE: 25
aagcagugca auguu                                                     15
```

REGULATION OF MESODERMAL SPECIFICATION

CLAIM OF PRIORITY

This application is a U.S. National Stage Filing under 35 U.S.C. § 371 of International Application No. PCT/US 2016/044859, filed 29 Jul. 2016 and Published as WO 201_7/020009 A1 on 2 Feb. 2017, which claims the benefit of priority of U.S. Provisional Patent Application No. 62/199,044, filed 30 Jul. 2015, the benefit of priority of which is claimed hereby, and which applications are incorporated by reference herein in their entirety.

GOVERNMENT GRANT SUPPORT

This invention was made with government support under U01HL100407 and R01AR064195 awarded by the National Institutes of Health. The government has certain rights in the invention.

BACKGROUND OF THE INVENTION

During embryogenesis mesodermal progenitors give rise to multiple lineages including hemato-endothelial and cardiac lineages. Precise control of the specification of these lineages are necessary for proper development and embryogenesis, although the transcriptional regulators and signaling pathways that govern mesodermal progenitors are incompletely defined (Kattman et al., 2006; Loebel et al., 2003).

Genetic studies have demonstrated the emergence of hematopoietic lineages, both independently, as well as from the hemogenic endothelium (Huber et al., 2004; Ueno and Weisman, 2006). Studies have established a hierarchy of transcriptional regulators, including Mesp1, Vegf/Flk1 and Etv2 as modulators of hemato-endothelial development (Shalaby et al., 1995; Saga et al., 1999; Ferdous et al., 2009). Genetic ablation of Etv2 results in embryonic lethality by E9.5 with complete absence of the hemato-endothelial lineages (Ferdous et al., 2009). Etv2 activates downstream targets including Tie2 and Lmo2 and interacts with Gata2 and FoxC2 to regulate the hemato-endothelial program (De Val et al., 2008; Rasmussen et al., 2011; Koyano-Nakagawa et al., 2012).

SUMMARY OF THE INVENTION

Described herein is a novel Etv2-miR-130a-Pdgfra network that directs stem cells, such as hemato-endothelial progenitors, towards the endothelial fate without affecting the hematopoietic lineage. This is the first report that defines a factor that directs endothelial development without affecting the hematopoietic lineage (directs cell fate to endothelium without effecting blood).

One embodiment provides a method to differentiate cells comprising contacting (in vitro and/or in vivo) stem, progenitor or precursor cells with miR-130a, or nucleic acid, such as, RNA having at least 95% identity thereto, so as to yield cells of endothelial lineage. In one embodiment, the stem, progenitor or precursor cells are embryonic stem cells, adult stem cells, induce pluripotent stem cells, and/or multipotent stem cells, such as multipotent mesodermal precursors. In another embodiment, the stem, progenitor or precursor cells are mammalian cells. In one embodiment, the progenitor cells are hemato-endothelial progenitors. In another embodiment, the precursor cells are mesodermal precursor cells expressing Flk1$^+$/Pdgfra$^+$.

One embodiment provides for admixing the endothelial lineage cells produced by the methods described herein with a pharmaceutically acceptable carrier.

One embodiment provides a method treat cardiovascular disease, a wound, and/or repopulate vasculature in a subject in need thereof comprising administering an effective amount of the endothelial lineage cells produced by the methods described herein so as to treat cardiovascular disease, a wound, and/or repopulate vasculature in said subject. In one embodiment, the administered cells are autologous or allogeneic.

One embodiment provides a composition consisting essentially of miR-130a and stem, progenitor and/or precursor cells. In one embodiment, the cells are mammalian.

One embodiment provides a composition comprising the endothelial lineage cells obtained by the methods described herein and a cell culture media or a pharmaceutically acceptable carrier.

One embodiment provides a method to differentiate stem, progenitor and/or precursor cells comprising contacting said stem, progenitor and/or precursor cells with Etv2, so as to increase expression of Flk1 and decrease expression of Pdgfra relative to the initial cell population and contacting said cells with increased expression Flk1 and decreased expression of Pdgfra with miR-130a so to generate cells predominately of endothelial lineages, while not generating a significant population of cells of the hematopoietic lineage.

Another embodiment provides a method to differentiate cells comprising contacting stem, progenitor and/or precursor cells with Etv2 and miR-130a so as to yield cells predominantly of endothelial lineages, while not yielding a significant population of cells of the hematopoietic lineage.

Another embodiment provides a method to differentiate cells comprising contacting stem, progenitor and/or precursor cells with miR-130a so as to yield cells predominantly of endothelial lineages, while not yielding a significant population of cells of the hematopoietic lineage.

In one embodiment, the stem, progenitor or precursor cells are embryonic stem cells, adult stem cells, induced pluripotent stem cells, and/or multipotent stem cells (such as multipotent mesodermal precursors). In one embodiment, the stem, progenitor or precursor cells are mammalian cells.

One embodiment provides for the admixing of the endothelial lineage cells described/prepared herein with a pharmaceutically acceptable carrier.

In one embodiment, the endothelial lineage cells described/prepared herein are administered to a subject.

One embodiment provides a composition of miR-130a and stem, progenitor and/or precursor cells. In one embodiment, the cells are mammalian.

Another embodiment provides a composition comprising the endothelial lineage cells obtained by the methods described herein and a cell culture media or a pharmaceutically acceptable carrier.

DETAILED DESCRIPTION OF THE INVENTION

Figure 1:
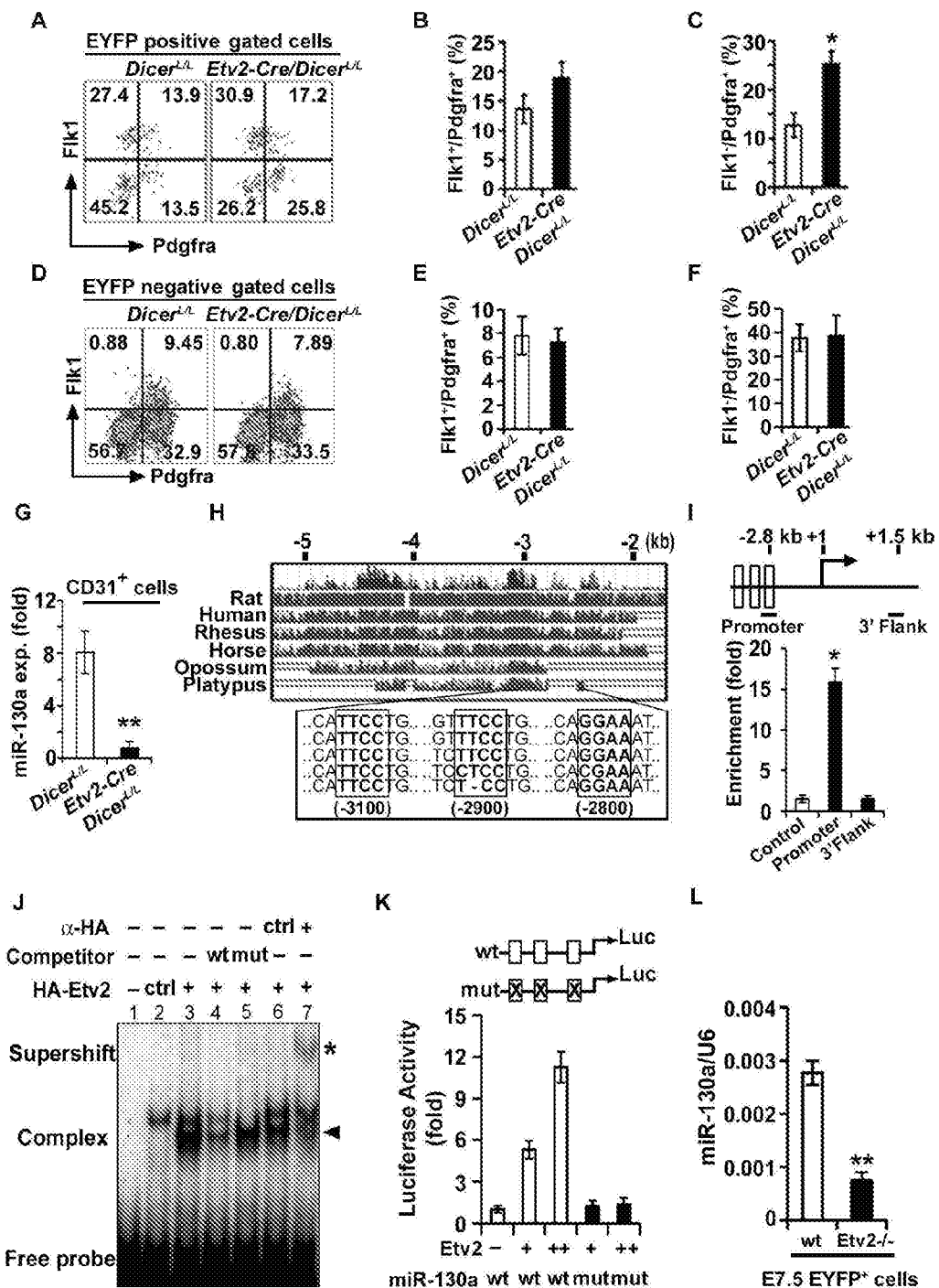
FIGS. 1A-L demonstrate that Etv2 modulates miR-130a expression in endothelial progenitors. (A-F) FACS profile (A, D) and quantification (B, C, E, F) of mesodermal populations in Etv2-EYFP::Etv2$^{Cre/+}$; Dicer$^{L/L}$ embryos at E7.5 from EYFP$^+$ and EYFP$^-$ compartments. (G) qPCR analysis of miR-130a in CD31$^+$ cells sorted from Dicer$^{L/L}$ and Etv2$^{Cre/+}$; Dicer$^{L/L}$ embryos at E9.5. (H) Evolutionary conservation of the 5.0 kb upstream fragment of the miR-130a gene. (I) Top: Schematic of the 2.8 kb upstream region of the miR-130a promoter. Bottom: ChIP analysis of d4 Dox-inducible HA-Etv2 EBs using an HA antibody. ChIP assay for the Gapdh promoter (Control) and a non-specific locus (miR-130a 3' UTR region; 3' Flank) are shown as controls. (J) EMSA showing Etv2 bound to the Ets binding site in the miR-130a promoter region. (K) Luciferase reporter constructs using the miR-130a promoter (−1.0 kb) harboring wild-type (wt; open box) or mutant (mut; crossed box) Etv2 binding sites. (L) qPCR analysis of miR-130a using EYFP$^+$ sorted cells from Etv2 wild-type and mutant embryos at E7.5. Error bars indicate SEM (n=4; *p<0.05; **p<0.005) (see also FIG. 5).

MicroRNAs (small non-coding RNAs) are known to regulate developmental stages during embryogenesis.

MicroRNAs (miRNAs) govern the molecular switch by suppressing gene expression, thereby modulating and fine-tuning cell fate decisions (Ivey and Srivastava, 2010). Although global deletion as well as hypomorphic mutants of Dicer (miRNA processing enzyme) results in embryonic lethality (Bernstein et al., 2003; Yang et al., 2005), it is unclear whether miRNAs play any role in the hemato-endothelial segregation and vascular development.

Herein is disclosed a novel Etv2-miR-130a cascade that regulates mesodermal specification and determination. Ablation of Dicer in the Etv2-expressing precursors resulted in altered mesodermal lineages and embryonic lethality by E12.5. miR-130a was identified as a direct target of Etv2 and demonstrated its role in the segregation of bipotent hemato-endothelial progenitors towards the endothelial lineage. Loss- and gain-of-function experiments demonstrated that miR-130a is a regulator of the endothelial program at the expense of cardiac program without impacting the hematopoietic lineages. Mechanistically, miR-130a directly suppresses expression level of Pdgfra and promotes the endothelial program by blocking Pdgfra signaling. Inhibition or activation of Pdgfra signaling phenocopied the miR-130a over-expression and knockdown, respectively. This is the first report of a miRNA that specifically promotes the divergence of the common hemato-endothelial progenitor to the endothelial lineage (miRNA mediated regulation of mesodermal precursors).

Definitions

The terminology used herein is for the purpose of describing particular embodiments only and is not intended to be limiting of the invention.

As used herein, the indefinite articles "a", "an" and "the" should be understood to include plural reference unless the context clearly indicates otherwise.

The phrase "and/or," as used herein, should be understood to mean "either or both" of the elements so conjoined, e.g., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, e.g., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

As used herein, the term "about" means plus or minus 10% of the indicated value. For example, about 100 means from 90 to 110.

The term "isolated" refers to a cell or cells which are not associated with one or more cells or one or more cellular components that are associated with the cell or cells in vivo.

A "subject" is a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, and orangutan) rat, sheep, goat, cow and bird. Subjects that can benefit from the cells and methods of the invention include, but are not limited to, those suffering from a loss of function of endodermal cells, including, but not limited to, liver or pancreatic cells, as a result of physical or disease related damage.

Totipotent (a.k.a. omnipotent) stem cells can differentiate into embryonic and extraembryonic cell types. Such cells can construct a complete, viable organism. These cells are produced from the fusion of an egg and sperm cell. Cells produced by the first few divisions of the fertilized egg are also totipotent. Pluripotent stem cells are the descendants of totipotent cells and can differentiate into nearly all cells, i.e. cells derived from any of the three germ layers. Multipotent stem cells can differentiate into a number of cell types, but only those of a closely related family of cells. Oligopotent stem cells can differentiate into only a few cell types, such as lymphoid or myeloid stem cells. Unipotent cells can produce only one cell type, their own,[4] but have the property of self-renewal, which distinguishes them from non-stem cells (e.g. progenitor cells, muscle stem cells).

"Expansion" refers to the propagation of cells without differentiation.

"Progenitor cells" are cells produced during differentiation of a stem cell that have some, but not all, of the characteristics of their terminally-differentiated progeny. Defined progenitor cells are committed to a lineage, but not to a specific or terminally-differentiated cell type. The phrase "endothelial cells" encompasses not only terminally-differentiated cells types, but also cells that are committed to an endothelial lineage, but are not terminally-differentiated.

"Differentiation factors" refer to cellular factors, preferably growth factors or angiogenic factors that induce lineage commitment.

"Self-renewal" refers to the ability to produce replicate daughter cells having differentiation potential that is identical to those from which they arose. A similar term used in this context is "proliferation."

An "effective amount" generally means an amount which provides the desired local or systemic effect and/or performance, particularly for treating a condition of interest.

The terms "comprises," "comprising," and the like can have the meaning ascribed to them in U.S. Patent Law and can mean "includes," "including" and the like. As used herein. "including" or "includes" or the like means including, without limitation.

Stem/Precursor/Progenitor Cells

Stem/Precursor/Progenitor cells are undifferentiated biological cells that can differentiate into specialized cells and can divide (through mitosis) to produce more stem cells. They are found in multicellular organisms. In adult organisms, stem cells and progenitor cells act as a repair system for the body, replenishing adult tissues. In a developing embryo, stem cells can differentiate into all the specialized cells-ectoderm, endoderm and mesoderm (see induced pluripotent stem cells)-but also maintain the normal turnover of regenerative organs, such as blood, skin, or intestinal tissues.

Autologous adult stem cells can be obtained from many sources in humans, such as bone marrow (which requires extraction by harvesting that is, drilling into bone (typically the femur or iliac crest); adipose tissue (lipid cells; which requires extraction, such as by liposuction); and/or blood (which requires extraction through apheresis, wherein blood is drawn from the donor (similar to a blood donation), and passed through a machine that extracts the stem cells and returns other portions of the blood to the donor). Heterologous and xenogeneic cells can also be used in methods of the invention.

Stem cells can also be taken from umbilical cord blood just after birth. By definition, autologous cells are obtained from one's own body, just as one may bank his or her own blood for elective surgical procedures.

In one embodiment, the precursor cells are multipotent mesodermal precursor cells expressing Flk1$^+$/Pdgfra$^+$.

Methods of isolating various stem and/or progenitor and/or precursor cells are available to an art worker. Stem and/or progenitor and/or precursor cells can also be isolated in the presence of various factors such as LIF (e.g., at a concentration of about 5,000 U/ml to about 50,000 U/ml, such as about 10,000 U/ml). EGF (e.g., at a concentration of about 5 ng/ml to about 50 ng/ml, such as about 10 ng/ml), basic FGF (e.g., at a concentration of about 5 ng/ml to about 50 ng/ml, such as about 10 ng/ml) or PDGF (e.g., at a concentration of about 5 ng/ml to about 50 ng/ml, such as about 10 ng/ml).

During and after isolation, stem and/or progenitor and/or precursor cells can be cultured in culture medium that is well established in the art and commercially available from the American Type Culture Collection (ATCC). Such media include, but are not limited to, Dulbecco's Modified Eagle's Medium (DMEM), DMEM F12 medium, Eagle's Minimum Essential Medium, F-12K medium, Iscove's Modified Dulbecco's Medium, or RPMI-1640 medium. It is within the skill of one in the art to modify or modulate concentrations of media and/or media supplements as needed for the cells used. It will also be apparent that many media are available as low-glucose formulations, with or without sodium pyruvate.

Also contemplated is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, rat serum (RS), serum replacements, and bovine embryonic fluid. It is understood that sera can be heat-inactivated at 55-65 µC if deemed necessary to inactivate components of the complement cascade. Modulation of serum concentrations, or withdrawal of serum from the culture medium can also be used to promote survival of one or more desired cell types. In one embodiment, the endodermal progenitor cells are cultured in the presence of FBS/or serum specific for the species cell type. For example, endodermal progenitor cells can be isolated and/or expanded with total serum (e.g., FBS) concentrations of about 0.5% to about 5% or greater including about 5% to about 15%. Concentrations of serum can be determined empirically.

Additional supplements can also be used to supply the cells with trace elements for optimal growth and expansion. Such supplements include insulin, transferrin, sodium selenium, and combinations thereof. These components can be included in a salt solution such as, but not limited to, Hanks' Balanced Salt Solution (HBSS), Earle's Salt Solution, antioxidant supplements. MCDB-201 supplements, phosphate buffered saline (PBS), N-2-hydroxyethylpiperazine-N'-ethanesulfonic acid (HEPES), nicotinamide, ascorbic acid and/or ascorbic acid-2-phosphate, as well as additional amino acids. Many cell culture media already contain amino acids; however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-inositol, L-isoleucine, L-leucine, L-lysine, L-methionine, L-phenylalanine, L-proline, L-serine, L-threonine, L-tryptophan, L-tyrosine, and L-valine.

Antibiotics are also typically used in cell culture to mitigate bacterial, mycoplasmal, and fungal contamination. Typically, antibiotics or anti-mycotic compounds used are mixtures of penicillin/streptomycin, but can also include, but are not limited to, amphotericin (Fungizone), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Hormones can also be advantageously used in cell culture and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine, β-mercaptoethanol can also be supplemented in cell culture media.

Lipids and lipid carriers can also be used to supplement cell culture media, depending on the type of cell and the fate of the differentiated cell. Such lipids and carriers can include, but are not limited to cyclodextrin, cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulation.

Also contemplated is the use of feeder cell layers. Feeder cells can be used to support the growth of cultured cells, including, stem and/or progenitor and/or precursor cells. Feeder cells are normal cells that have been inactivated by γ-irradiation. In culture, the feeder layer serves as a basal layer for other cells and supplies cellular factors without further growth or division of their own (Lim and Bodnar 2002). Examples of feeder layer cells typically used with liver cell cultures are hepatocytes and embryonic fibroblasts (Suzuki, A. et al. 2000), but can be any post-mitotic cell that is capable of supplying cellular components and factors that are advantageous in allowing optimal growth, viability, and expansion of, stem and/or progenitor and/or precursor cells. In some cases, feeder cell layers are not needed to keep cells in an undifferentiated, proliferative state, as leukemia inhibitory factor (LIF) has anti-differentiation properties. Often, supplementation of a defined concentration of LIF is all that is necessary to maintain cells in an undifferentiated state.

Cells in culture can be maintained either in suspension or attached to a solid support, such as extracellular matrix components and synthetic or biopolymers. Cells often require additional factors that encourage their attachment to a solid support (e.g., attachment factors) such as type I, type II, and type IV collagen, concanavalin A, chondroitin sulfate, fibronectin, "superfibronectin" and/or fibronectin-like polymers, gelatin, laminin, poly-D and poly-L-lysine, Matrigel, thrombospondin, and/or vitronectin.

The maintenance conditions of cells can also contain cellular factors that allow cells, such as stem and/or progenitor and/or precursor cells, to remain in an undifferentiated form. It may be advantageous under conditions where the cell must remain in an undifferentiated state of self-renewal for the medium to contain epidermal growth factor (EGF), platelet derived growth factor (PDGF), leukemia inhibitory factor (LIF), basic fibroblast growth factor (bFGF) and combinations thereof. It is apparent to those skilled in the art that supplements that allow the cell to self-renew (e.g., to produce replicate daughter cells having differentiation potential that is identical to those from which they arose; a similar term used in this context is "proliferation"), but not differentiate should be removed from the culture medium prior to differentiation. It is also apparent that not all cells will require these factors. In fact, these factors may elicit unwanted effects, depending on the cell type.

Stem and/or progenitor and/or precursor cells can be selected based on the markers (gene and/or protein) described herein. Accordingly, positive selection methods can be used, either alone or together with the methods described above, to identify and/or isolate the cells of the invention. Methods of positive selection can include visual selection, using microscopy and/or other means of detection, including, but not limited to, immunoblotting, immunofluorescence, and/or enzyme-linked immunosorbent assay. Other methods of positive selection can also include, but are not limited to, additional selective culture techniques (e.g., variable cell densities or amounts of $CO_2$), flow cytometry, RT-PCR, and/or microchip-based methods of cell separation.

Endothelium

The endothelium is the thin layer of simple squamous cells that lines the interior surface of blood vessels and lymphatic vessels, forming an interface between circulating blood or lymph in the lumen and the rest of the vessel wall. The cells that form the endothelium are called endothelial cells. Endothelial cells in direct contact with blood are called vascular endothelial cells, whereas those in direct contact with lymph are known as lymphatic endothelial cells.

Vascular endothelial cells line the entire circulatory system, from the heart to the smallest capillaries. These cells have unique functions in vascular biology. These functions include fluid filtration, such as in the glomeruli of the kidney, blood vessel tone, hemostasis, neutrophil recruitment, and hormone trafficking. Endothelium of the interior surfaces of the heart chambers is called endocardium.

Endothelium is mesodermal in origin. Both blood and lymphatic capillaries are composed of a single layer of endothelial cells called a monolayer. In straight sections of a blood vessel, vascular endothelial cells typically align and elongate in the direction of fluid flow.

The foundational model of anatomy makes a distinction between endothelial cells and epithelial cells on the basis of which tissues they develop from, and states that the presence of vimentin rather than keratin filaments separate these from epithelial cells.

Endothelial cells are involved in many aspects of vascular biology, including: barrier function (the endothelium acts as a semi-selective barrier between the vessel lumen and surrounding tissue, controlling the passage of materials and the transit of white blood cells into and out of the bloodstream; Excessive or prolonged increases in permeability of the endothelial monolayer, as in cases of chronic inflammation, may lead to tissue edema/swelling); blood clotting (thrombosis & fibrinolysis; the endothelium normally provides a non-thrombogenic surface because it contains, for example, heparan sulfate which acts as a cofactor for activating antithrombin, a protease that inactivates several factors in the coagulation cascade); inflammation; formation of new blood vessels (angiogenesis); vasoconstriction and vasodilation (and hence the control of blood pressure); repair of damaged or diseased organs via an injection of blood vessel cells; and angiopoietin-2 works with VEGF to facilitate cell proliferation and migration of endothelial cells.

Endothelial dysfunction, or the loss of proper endothelial function, is a hallmark for vascular diseases, and is often regarded as a key early event in the development of atherosclerosis. Impaired endothelial function, causing hypertension and thrombosis, is often seen in patients with coronary artery disease, diabetes mellitus, hypertension, hypercholesterolemia, as well as in smokers. Endothelial dysfunction has also been shown to be predictive of future adverse cardiovascular events, and is also present in inflammatory disease such as rheumatoid arthritis and systemic lupus erythematosus. One of the main mechanisms of endothelial dysfunction is the diminishing of nitric oxide, often due to high levels of asymmetric dimethylarginine, which interfere with the normal L-arginine-stimulated nitric oxide synthesis and so leads to hypertension. The most prevailing mechanism of endothelial dysfunction is an increase in reactive oxygen species, which can impair nitric oxide production and activity via several mechanisms. The signaling protein ERK5 plays a role in maintaining normal endothelial cell function. A further consequence of damage to the endothelium is the release of pathological quantities of von Willebrand factor, which promote platelet aggregation and adhesion to the sub-endothelium, and thus the formation of thrombi.

Differentiation and Use for Endothelial Cells

Stem, precursor and progenitor cells can be used for the generation of endothelial cells or endothelia precursors (the term endothelial cells refers to cells of varying degree of differentiation, some may be fully differentiated down the endothelial pathway, while others are in the early stages and can still be directed down one or endothelial lineages). One embodiment provides methods for providing endothelial cells comprising differentiating stem, precursor and progenitor cells in the presence of miR-130a and optionally Etv2 (sequence information provided in Example 2 below), and isolating the endothelial cells. Differentiation can occur in vitro, in vivo or ex vivo.

miR-130 microRNA precursor is a small non-coding RNA that regulates gene expression. This microRNA has been identified in mouse (MI0000156 (GAGCUCUUUU-CACAUUGUGCUACUGUCUAACGUGUAC-CGAGCAGU GCAAUGUUAAAAGGGCAUC; SEQ ID NO:1), MI0000408 (GGCUUGUUGGACACUCUUUC-CCUGUUGCACUACUGUGGGCCUCUG CGGAAGCA-GUGCAAUGAUGAAAGGGCAUCUGUCCGGGCC; SEQ ID NO:2)), and in human (MI0000448 (UGCUGCUG-GCCAGAGCUCUUUUCACAUUGUGCUACUGUCUG-CACC UGUCACUAGCAGUGCAAU-GUUAAAAGGGCAUUGGCCGUGUAGUG; SEQ ID NO:3), MI0000748 (GGCCUGCCCGACACUCUUUC-CCUGUUGCACUACUAUAGGCCGCUG GGAAGCA-GUGCAAUGAUGAAAGCCjCAUCGGUCAGGUC; SEQ ID NO:4)). Mentioned below is the seed sequence for miR-130a. The data is obtained from the mirbase (http//www.mirbase.org)>mmu-miR-130a-3p MIMAT0000141-CAGUGCAAUGUUAAAAGGGCAU (SEQ ID NO:5) (the seed sequence for miR-130 can be used as a screening tool to search and/or engineer small molecules that bind/interact with the seed sequence and cause the effect of, for example, increased endothelium, as with miR-130).

In one embodiment, the miR-130 is as disclosed herein or 95% identical thereto. IN another embodiment, the mirNA-130 has at least about 85%, 86%, 87%, 88%, 89%, 90%, 91%, 92%, 93%, 94%, 95%, 96%, 97%, 98%, 99%, or 99.5% identity to the nucleic acid sequences disclosed herein.

As used herein, percent identity of two nucleic acid sequences (or of two amino acid sequences) is determined using the algorithm of Karlin and Altschul (PNAS USA 87:2264-2268, 1990), modified as in Karlin and Altschul, PNAS USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al. (Nucleic Acids Res. 25:3389-3402, 1997). When utilizing BLAST and GappedBLAST programs the default parameters of the respective programs (e.g., XBLAST and NBLAST) are used to obtain nucleotide sequences homologous to a nucleic acid molecule of the invention.

Identity or identical means nucleic acid sequence (or amino acid sequence) similarity and has an art recognized meaning. Sequences with identity share identical or similar amino acids (or nucleic acids). Sequence identity is the percentage of amino acids identical to those in the antibody's original amino acid sequence, determined after the sequences are aligned and gaps are appropriately introduced to maximize the sequence identity as necessary. Thus, a candidate sequence sharing 85% amino acid sequence identity with a reference sequence requires that, following alignment of the candidate sequence with the reference sequence, 85% of the amino acids in the candidate sequence are identical to the corresponding amino acids in the reference sequence, and/or constitute conservative amino acid changes.

miR-130 appears to be vertebrate-specific miRNA and has now been predicted or experimentally confirmed in a range of vertebrate species (MIPF0000034). Mature microRNAs are processed from the precursor stem-loop by the Dicer enzyme. In this case, the mature sequence is excised from the 3' arm of the hairpin. It has been found that miR-130 is upregulated in a type of cancer called hepatocellular carcinoma.

Methods of identifying and subsequently isolating differentiated cells from their undifferentiated counterparts can be carried out by methods available to an art worker. Cells that have been induced to differentiate can be identified by selectively culturing cells under conditions whereby differentiated cells outnumber undifferentiated cells. These conditions include, for example, extending the amount of time that cells are grown in culture, such that survival of a desired cell type is encouraged. Many primary cells achieve senescence, and fail to divide, or die, after a period of time. Other conditions comprise modulating the type and concentration of serum, or culturing the cells in the presence or absence of growth factors and/or cytokines that induce differentiation to another cell type. Differentiation can also be advantageously achieved by modulation of serum concentrations, or withdrawal of serum from the culture. Other methods of inducing differentiation can include, but are not limited to, modulating the acidity of the culture medium, as well as the oxygen and carbon dioxide levels during culture.

Similarly, differentiated cells can be identified by morphological changes and characteristics that are not present on their undifferentiated counterparts, such as cell size, the number of cellular processes (i.e., formation of dendrites and/or branches), and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS), and/or enzyme-linked immunosorbent assay (ELISA). From the standpoint of transcriptional upregulation of specific genes, differentiated cells often display levels of gene expression that are different from undifferentiated cells. Reverse-transcription polymerase chain reaction (RT-PCR) can also be used to monitor changes in gene expression in response to differentiation. In addition, whole genome analysis using microarray technology can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads, and combinations thereof. One embodiment of the invention envisions the use of FACS to identify and separate cells based on cell-surface antigen expression.

Administration/Treatment

Endothelial cells of the invention can be used in cell replacement therapies. Endothelial cells can be administered to a tissue of interest in a subject to supplement functioning cells or replace cells, which have lost function. Alternatively, methods of providing differentiated cells are also contemplated, wherein the endothelial cells are differentiated in the presence of differentiation factors, isolated, and administered into or upon the body of a subject.

For the purposes described herein, either autologous, allogeneic or xenogeneic cells can be administered to a patient, either in undifferentiated, terminally differentiated or in a partially differentiated form, genetically altered or unaltered, by direct introduction to a site of interest, e.g., on or around the surface of an acceptable matrix, or systemically, in combination with a pharmaceutically acceptable carrier so as to repair, replace or promote the growth of existing and/or new blood vessels.

Disease states could benefit from endothelial cells and methods of the invention include, but are not limited to, cardiovascular disease, wound healing, and/or repopulation or engineering vasculature in vitro and/or in vivo.

Exogenous factors (e.g., cytokines, differentiation factors and other factors) can be administered prior to, after or concomitantly with the endothelial cells of the invention. For example, a form of concomitant administration would comprise combining a factor of interest in the culture media and/or pharmaceutically acceptable carrier prior to administration. Doses for administrations are variable, may include an initial administration followed by subsequent administrations; but nonetheless, can be ascertained by the skilled artisan, from this disclosure, the documents cited herein, and the knowledge in the art.

Endothelial cells of the invention or their progeny can be administered via localized injection, including catheter administration, systemic injection, localized injection, parenteral administration, or intrauterine injection into an embryo.

A method to potentially increase cell survival, when introducing the cells into a subject in need thereof, is to incorporate endothelial cells into a biopolymer or synthetic polymer. Depending on the subject's condition, the site of injection might prove inhospitable for cell seeding and growth because of scarring or other impediments. Examples of biopolymer include, but are not limited to, cells mixed with fibronectin, fibrin, fibrinogen, thrombin, collagen, and proteoglycans. This could be constructed with or without included cytokines, growth factors, differentiation factors or nucleic acid expression constructs. Additionally, these could be in suspension, but residence time at sites subjected to flow would be nominal. Another alternative is a three-dimensional gel with cells entrapped within the interstices of the cell biopolymer admixture. Again, differentiation factors, growth factors or cytokines could be included within the cells. These could be deployed by injection via various routes described herein.

A parameter involved in the therapeutic use of endothelial cells is the quantity of cells necessary to achieve an optimal effect. In current human studies of autologous mononuclear bone marrow cells, empirical doses ranging from 1 to $4\times10^7$ cells have been used with encouraging results. However, different scenarios may require optimization of the amount of cells injected into a tissue of interest. Thus, the quantity of cells to be administered will vary for the subject being treated. In one embodiment, between $10^4$ to $10^8$, more preferably $10^5$ to $10^7$, and most preferably $3\times10^7$ progenitor cells and optionally, 50 to 500 µg/kg per day of a cytokine can be administered to a human subject. However, the precise determination of what would be considered an effective dose may be based on factors individual to each patient, including their size, age, size tissue damage, and amount of time since the damage occurred. Therefore, dosages can be readily ascertained by those skilled in the art from this disclosure and the knowledge in the art.

Another parameter involved in the use of endothelial cells is the purity of the population. Those skilled in the art can readily determine the percentage of endothelial cells in a population using various well-known methods, such as fluorescence activated cell sorting (FACS). Preferable ranges of purity in populations comprising endothelial cells are about 1 to about 5%, about 5 to about 10%, about 10 to about 15%, about 15 to about 20%, about 20 to about 25%, about 25 to about 30%, about 30 to about 35%, about 35 to about 40%, about 40 to about 45%, about 45 to about 50%, about 50 to about 55%, about 55 to about 60%, about 60 to about 65%, about 65 to about 70%, about 70 to about 75%, about 75 to about 80%, about 80 to about 85%, about 85 to about 90%, about 90 to about 95% or about 95 to about 100%. Purity of the cells can be determined according to the cell surface marker profile within a population. Dosages can be readily adjusted by those skilled in the art (e.g., a decrease in purity may require an increase in dosage).

The skilled artisan can readily determine the amount of cells and optional additives, vehicles, and/or carrier in compositions to be administered in methods of the invention. Typically, any additives (in addition to the active cell(s) and/or cytokine(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Of course, for any composition to be administered to an animal or human, and for any particular method of administration, it is preferred to determine the toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

When administering a therapeutic composition of the present invention, it will generally be formulated in a unit dosage injectable form (solution, suspension, emulsion) However, the cells can be administered to a subject by a variety of methods available to the art, including but not limited to localized injection, catheter administration, systemic injection, intraperitoneal injection parenteral administration, oral administration, intracranial injection, intraarterial injection, intravenous injection, intraventricular infusion, intraplacental injection, intrauterine injection, surgical intramyocardial injection, transendocardial injection transvascular injection, intracoronary injection, transvascular injection, intramuscular injection, surgical injection into a tissue of interest or via direct application to tissue surfaces (e.g., during surgery or on a wound). The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired. Examples of compositions comprising progenitor cells of the invention include liquid preparations for administration, including suspensions; and, preparations for intramuscular or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, which is incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (e.g., purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes.

Viscosity of the compositions, if desired, can be maintained at the selected level using a pharmaceutically acceptable thickening agent. Methylcellulose is readily and economically available and is easy to work with. Other suitable thickening agents include, for example, xanthan gum, carboxymethyl cellulose, hydroxypropyl cellulose, carbomer, and the like. The concentration of the thickener will depend upon the agent selected. The point is to use an amount, which will achieve the selected viscosity. Viscous compositions are normally prepared from solutions by the addition of such thickening agents.

A pharmaceutically acceptable preservative or cell stabilizer can be employed to increase the life of the compositions. If preservatives are used, it is well within the purview of the skilled artisan to select compositions that will not affect the viability or efficacy of the endodermal progenitor cells as described herein.

Those skilled in the art will recognize that the components of the compositions should be selected to be chemically inert. This will present no problem to those skilled in chemical and pharmaceutical principles, or problems can be readily avoided by reference to standard texts or by simple experiments (not involving undue experimentation), from this disclosure and the documents cited herein.

Compositions can be administered in dosages and by techniques well known to those skilled in the medical and veterinary arts taking into consideration such factors as the age, sex, weight, and condition of the particular patient, and the composition form used for administration (e.g., solid vs. liquid). Dosages for humans or other mammals can be determined without undue experimentation by the skilled artisan, from this disclosure, the documents cited herein, and the knowledge in the art.

Suitable regimes for initial administration and further doses or for sequential administrations also are variable and may include an initial administration followed by subsequent administrations; but nonetheless, can be ascertained by the skilled artisan, from this disclosure, the documents cited herein, and the knowledge in the art.

Endothelial cells of the invention can be used for many diverse clinical and pre-clinical applications, which can include, but are not limited to, use in toxicological or genomic screening methods, determination of levels of enzymes and coagulation factors, as well as treatment of the diseases disclosed herein. Endothelial cells of the invention can provide a variety of differentiated cultured cell types for high-throughput toxicological or genomic screening. The cells can be cultured in, for example, 96-well or other multi-well culture plates to provide a system for high-throughput screening of, for example, target cytokines, chemokines, growth factors, or pharmaceutical compositions in pharmacogenomics or pharmacogenetics.

The invention also envisions a tissue-engineered organ, or portion, or specific section thereof, a tissue engineered device comprising a tissue of interest and optionally, cytokines, growth factors, or differentiation factors that induce differentiation into a desired cell type, wherein the endothelial cells are used to generate tissue/vasculature.

The following examples are provided in order to demonstrate and further illustrate certain embodiments and aspects of the present invention and is not to be construed as limiting the scope thereof.

Examples

Materials and Methods
Generation of Dicer Conditional Null Mice and Morphological Analysis Dicer$^{L/L}$ mice (strain: B6.Cg-Dicer$^{tm1Bdh}$/J) (Harfe et al., 2005) were intercrossed with Mesp1-Cre (Saga et al., 1999), Flk1-Cre (Shalaby et al., 1995) and Etv2-Cre (Rasmussen et al., 2011) mice to generate Mesp1$^{Cre/+}$; Dicer$^{L/+}$, Flk1$^{Cre/+}$; Dicer$^{L/+}$ and Etv2$^{Cre/+}$; Dicer$^{L/+}$ mice and subsequently crossed with Dicer$^{L/L}$ mice to generate conditional Dicer knockouts.

Generation of Doxycycline-Inducible miR-130a Mouse ESC Line, Inducible Pdgfra ESC Lines, ES/EB Culture Conditions and FACS Analysis ESC culture conditions ES/EB differentiation and the generation of the Dox-inducible miR-130a ESCs were performed as previously reported (Iacovino et al., 2011).

ESC Culture and ES/EB Differentiation

The wild-type mouse E14 ES cell line was maintained in Knockout Medium (Invitrogen) supplemented with 15% FBS (Benchmark), 1000 U/ml LIF (Millipore), glutamine (Hyclone), 0.1 mM non-essential amino acids (NEAA) and 0.1 mM β-mercaptoethanol (Sigma) in gelatin-coated tissue-culture plates. The ES cells were differentiated into embryoid bodies (EBs) by the hanging drop method using mesodermal differentiation media containing IMDM (Invitrogen), 15% FBS, penicillin/streptomycin, 2 mM GlutaMAX, 50 mg/ml Fe-saturated transferrin (R & D Systems), 0.1 mM monothioglycerol (Sigma), and 50 mg/ml ascorbic acid (Sigma). Cryosectioning and immunohistochemical analyses were performed using a standard protocol with anti-TnT (1:200, Sigma) and anti-CD31 (1:200, BD Pharmingen) sera.

Flow Cytometry Analysis and Sorting

FACS analysis was performed using a BD FACSAriaII (BD Biosciences, San Diego, Calif., USA). Stage specific embryos were separated from yolk sacs, and digested with 0.25% trypsin (Hyclone) to obtain a single cell suspension. Cells were incubated with antibody cocktails for 30 minutes at 4° C., washed, and resuspended in PBS with 2% FBS. Cocktails of antibodies including Flk1-APC (eBiosciences 17-5821), Pdgfra-PE (eBiosciences 12-1401). CD31-APC (eBiosciences 25-0311), CD41-PECy7 (eBiosciences 25-0411), CD45-PE (BD Pharmingen 553081), CD31-PE (BD Pharmingen). VE-cadherin (BD Pharmingen) were used in this study. For the FACS analysis of EYFP+ cells, embryos were digested and cells were sorted based on EYFP fluorescence. For EBs, single-cell suspensions were incubated with the desired antibody combinations, washed and resuspended in FACS buffer (PBS/1% FBS). Cells were analyzed or sorted using FACSAria (BD Biosciences). FACS data were quantified using data obtained from four independent experiments.

RNA Isolation and Quantitative Gene Expression Analysis

Total RNA was isolated from embryos and EBs at various time-periods using miRVANA RNA isolation kit (Ambion), and cDNA was synthesized using superscript cDNA synthesis kit (Invitrogen). Quantitative RT-PCR was performed using ABI Taqman probe sets. Probes used in these studies include the following: VIC-labeled GAPDH:4352339E, FAM-labeled U6 snRNA: 001973; hsa-miR-130a: 000454; Flk1:mm00440099_m1, PECAM: mm01246167_m1, Tie2: mm01256892_m1, Tnnt2:mm00441922_m1, c-kit: mm00445212_m1, Lmo2: mm00493153_m1, CD41: mm00439741_m1, and Dicer: Mm00521722_m1.

Electrophoretic Mobility Shift Assay (EMSA)

Experimental details for performing EMSA were previously described (Koyano-Nakagawa et al., 2012). The oligonucleotides harboring the Etv2 binding motif in the miR-130a promoter region were; sense strand: 5'-GAATATAGGCAGGAAATTGACCAGAT-3' (SEQ ID NO:6); and antisense strand: 5'-ATCTGGTCAATTTCCT-GCCTATATTC-3'(SEQ ID NO:7).

Cell Transfection and Luciferase Assays

COS7 cells were transfected using Lipofectamine 2000 (Invitrogen) according to the manufacturer's protocols. For the luciferase transactivation assay, $0.5 \times 10^5$ cells were cultured in 24-well plates and transfected at 90% confluency with 0.25 µg/well of reporter construct together with increasing amounts of Etv2 constructs. pRL-TK (50 ng) was used as a control for transfection efficiency. Cells were analyzed at 24 hr posttransfection. Activities of firefly and *Renilla* luciferases were measured sequentially using the Dual-Luciferase Reporter Assay system (Promega) and a luminometer (Berthold Detection Systems, Sirius). For the miR-130a target assay, COS7 cells were transfected using Lipofectamine 2000 (Invitrogen) with 150 nM/well of miR-130a mimics/antagomir and 0.2 g/well of Pdgfra constructs. pRL-TK (20 ng) was used as a control for transfection efficiency. Transfected cells were harvested after 48 hr using the Dual-Luciferase Reporter Assay system (Promega). Luciferase activities were expressed in relative light units that were normalized to the transfection efficiency using the *Renilla* luciferase activity.

CFC Assay Using miR-130a IESCs

For the CFC assays, miR-130a iESCs were differentiated in the mesoderm-inducing condition and treated from Days 2-6 with doxycycline. For the lineage committed CFC assay, Flk$^+$/Pdgfra$^-$ (hemato-endothelial mesoderm) and Flk$^+$/Pdgfra$^+$ (unpatterned mesoderm and prospective cardiac mesoderm) were sorted at day 3.5 of EB differentiation without Dox. Sorted cells were reaggregated for an additional two days in the presence or absence of Dox. 50,000 dissociated cells from whole EBs or FACS sorted EBs were plated on a 35 mm culture dish with 1.5 ml of MethoCult (M3434, Stem Cell Technologies) according to the manufacturer's instructions. Hematopoietic colonies were identified and quantified after 10 days of incubation. These assays were performed in triplicate and independently repeated three times.

Reaggregation Assay

Reaggregation of the sorted cells was performed as described (Kouskoff et al., 2005). Briefly, $4 \times 10^5$ FACS-sorted cells were plated in a low attachment 24-well plate (Costar) containing EB differentiation media in the absence or the presence of Dox. Reaggregated EBs were FACS analyzed at day 6 as previously described (Rasmussen et al., 2011). These assays were repeated at least three times and statistical analysis was performed using Student's t-test.

ChiP Assay

The DNA-protein complex was immunoprecipitated with anti-HA serum (Santa Cruz, sc-805) from cell lysates using inducible HA-Etv2 EBs at day 3 of differentiation. qPCR was performed to detect the target region using the indicated primers; Fwd: 5'-GCTTTGGGTGAGGCTAAAACG-3' (SEQ ID NO:8); Rev: 5'-CAGAACCCCTGTTCCCA-GATG-3' (SEQ ID NO:9).

miR-130a Antagomir Transfection

Transfection of miR-130a antagomirs were performed as previously described (Zhang et al., 2014) with minor modifications. Briefly, ES cell suspensions were treated with 150 nM of control or miR-130a antagomirs together with RNAimax reagent (Invitrogen) in low-attachment 6-well plates (Costar). EBs were incubated with these oligonucleotides in a shaking culture and FACS assay was performed on d6 of EB differentiation.

Generation of Inducible Pdgfra ES Cell Lines

Lentiviruses expressing full-length of Pdgfra (Image-Clone 5704645. Open Biosystems) were generated and infected into A2lox as well as miR-130a iES clones. Viral infected cells were FACS sorted for EGFP$^+$ fluorescence after addition of Dox. Sorted GFP$^+$ cells were amplified and experiments were performed as described in the results section.

Zebrafish Morpholino and In Situ Hybridization Experiments

The following antisense MO oligonucleotides were designed by and obtained from the Gene Tools LLC. miR-130a-MO: 5'-CAATGCCCTTTTAACATTGCACTGC-3' (SEQ ID NO:10) miR-130a mis-MO: 5'-CAATaCCaTTT-TAAaATTaCACTaC-3'(SEQ ID NO:11) (lower case represents mismatch bases).

Wild-type and transgenic zebrafish lines, Tg(fli1a:GFP) (Motoike et al., 2003) were maintained according to the IACUC, UMN approved protocols. Zebrafish embryos at the one-two cell stage were injected with 25 ng mismatch control or miR-130a morpholinos following a standard procedure (Akiyama et al., 2014). The following antisense MO oligonucleotides were designed by and obtained from the Gene Tools LLC. miR-130a-MO: 5'-CAATGCCCTTT-TAACATTGCACTGC-3' (SEQ ID NO:12) miR-130a mis-MO: 5'-CAATaCCaTTTTAAaATTaCACTaC-3' (SEQ ID NO:13) (lower case represents mismatch bases). Whole mount in situ hybridization for Pdgfra was done using standard procedures as described previously (Ng et al., 2002). For the zebrafish in situ hybridization experiments, 25-30 embryos were examined for each set.

Morphological Analysis

For morphological analysis, embryos from time-mated females were harvested at specified stages. Embryos were fixed in 4% PFA overnight at 4° C. and imaged using the Zeiss Axio Observer Z1 inverted microscope.

Statistical Analysis

All experiments were repeated at least three times and the data represent the mean±SEM. Statistical significance was determined using the Student's t-test and a p-value<0.05 was considered as a significant change.

Results

Figure 5:
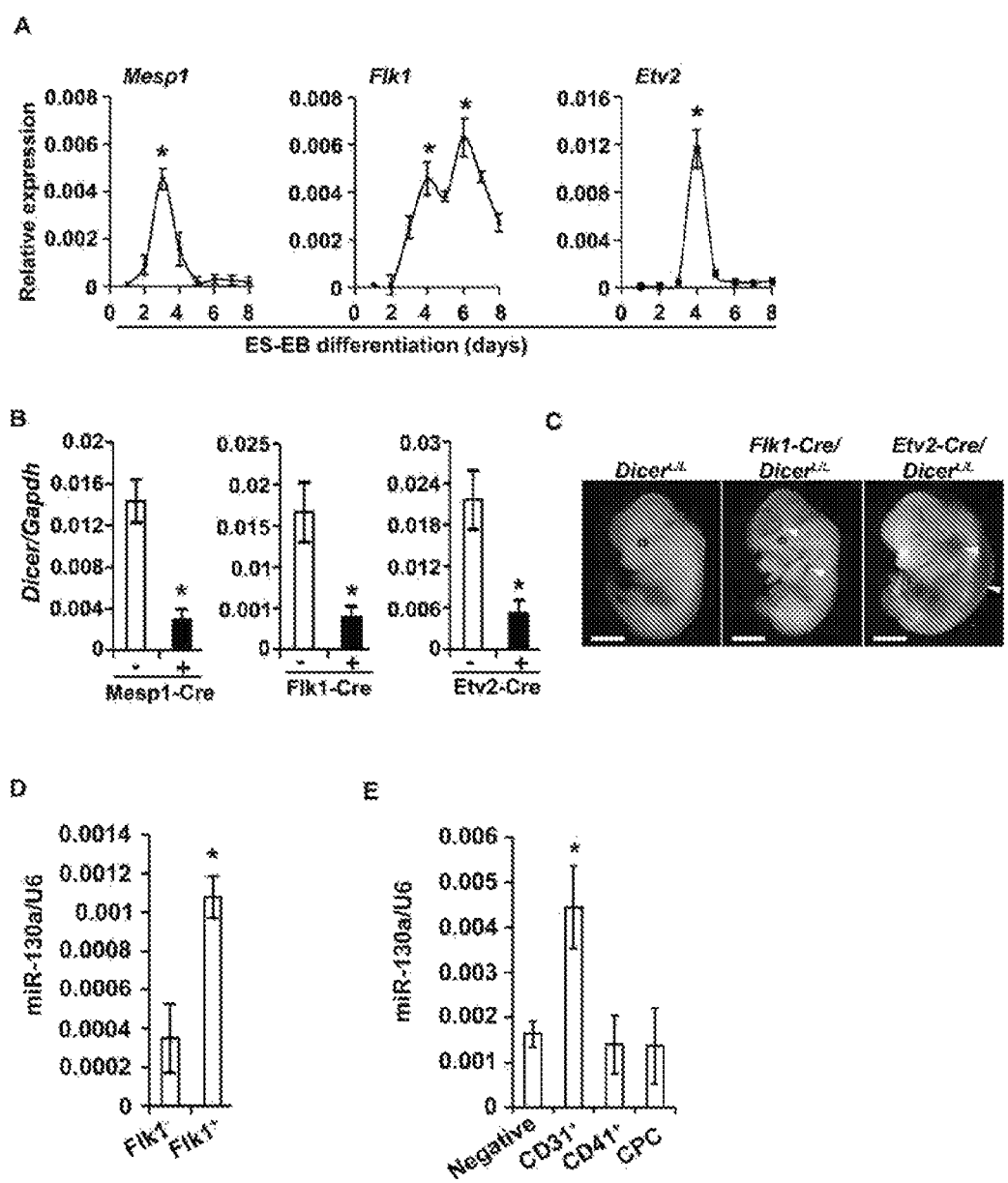
FIGS. 5A-E are related to FIG. 1; miR-130a is highly enriched in endothelial progenitors. (A) qRT-PCR analysis for Mesp1, Flk1 and Etv2 transcripts using RNA isolated from differentiating EBs. Expression was normalized to Gapdh levels. (B) qRTPCR for Dicer using primers directed to the RNase III domain. Mesp1 and Flk1 expressing cells were sorted using ROR2 (Drukker et al., 2012) and Flk1 antibodies, respectively. Etv2 expressing cells were sorted using EYFP fluorescence obtained from Etv2$^{Cre/+}$; Dicer$^{L/+}$ and Etv2-EYFP; Dicer$^{L/L}$ crosses at E8.5. (C) Whole mount images of Flk1$^{Cre/+}$; Dicer$^{L/L}$ and Etv2$^{Cre/+}$; Dicer$^{L/L}$ mutant embryos demonstrated edema, hemorrhage (arrowheads) and were lethal by E12.5. (D) qPCR of mature miR-130a using RNA isolated from FACS sorted Flk1$^+$ and Flk1$^-$ cells from EBs at day 4 of differentiation. (E) qPCR of mature miR-130a using RNA isolated from FACS sorted CD31$^+$, CD41$^+$, CPC (Nkx2.5-GFP) and negative cell populations at E9.5. Error bars indicate SEM (n=3; *p<0.05). Scale bar: 2 mm.

Etv2-Cre-Mediated Dicer Deletion Results in Altered Mesodermal Lineages and Embryonic Lethality Analysis of mesodermal transcripts during embryonic stem cell/embryoid body (ES/EB) differentiation indicated that Mesp1 was transiently, but robustly expressed at day (d) 3, with subsequent expression of both Flk1 and Etv2 at d4, marking the appearance of the mesodermal lineages (FIG. 5A). To examine the requirement for miRNAs in the mesodermal progenitors, floxed-Dicer was conditionally deleted in Mesp1, Flk1 and Etv2-expressing precursors using Cre recombinase under the control of either Mesp1, Flk1 and Etv2 promoter elements. qPCR analysis revealed efficient deletion of the Dicer allele from the FACS-sorted cells (FIG. 5B). Whole mount analysis revealed embryonic lethality in Mesp1$^{Cre/+}$; Dicer$^{L/L}$ embryos by E10.5; and the Flk1$^{Cre/+}$; Dicer$^{L/L}$ and the Etv2$^{Cre/+}$; Dicer$^{L/L}$ embryos were lethal by E12.5 due to vascular defects (FIG. 5C, Table 1).

Table 1 (related to FIG. 1). Dicer functions are needed in mesodermal progenitors. Table showing embryonic lethality at distinct developmental stages of conditional knockout embryos obtained from Mesp1-Cre, Flk1-Cre and Etv2-Cre mediated Dicer deletions.

| Stages | Mesp1-Cre/Dicer$^{L/L}$ (obs/exp) | Total | Flk1-Cre/Dicer$^{L/L}$ (obs/exp) | Total | Etv2-Cre/Dicer$^{L/L}$ (obs/exp) | Total |
|---|---|---|---|---|---|---|
| E8.5 | 6/6 | 22 | 5/4 | 16 | 12/12 | 47 |
| E9.5 | 6/7 | 30 | 3/3 | 12 | 16/17 | 70 |
| E12.5 | 1/9 | 36 | 2/6 | 25 | 10/25 | 98 |
| P1 | 0/12 | 48 | 0/17 | 68 | 0/16 | 64 |

These results indicated a need for miRNAs in the endothelial lineage. Previous studies analyzing Tie2$^{Cre/+}$; Dicer$^{L/L}$ or VE-Cad$^{Cre/+}$; Dicer$^{L/L}$ conditional mutants revealed viable animals with no obvious vascular defects (Saurez et al., 2007). Based on the findings and these reports, it is believed that miRNAs induced during Flk1 and Etv2 expression are needed for endothelial development.

Etv2 marks the earliest hemato-endothelial progenitors (Koyano-Nakagawa et al., 2012). Previous studies have demonstrated that Etv2-mutants have altered mesodermal populations (Rasmussen et al., 2011). To evaluate whether mesodermal derivatives were affected in Etv2$^{Cre/+}$; Dicer$^{L/L}$ mutants, Etv2$^{Cre/+}$; Dicer$^{L/+}$ and Etv2-EYFP; Dicer$^{L/L}$ lines were crossed and FACS analysis performed at E7.5. Etv2-EYFP reporter has been shown to label the hemato-endothelial lineages during embryogenesis (Rasmussen et al., 2011). The analysis showed a significant increase in the number of the Flk1−/Pdgfra+ cells in the Dicer conditional mutants (FIGS. 1A-C). In contrast, in the EYFP-fractions, no changes in the Flk1$^-$/Pdgfr$^+$ or Flk1$^+$/Pdgfr$^+$ populations were observed (FIGS. 1D-F). These results indicated that miRNAs that are expressed in the Etv2$^+$ progenitors are needed for segregation of the mesodermal lineages.

Figure 2:
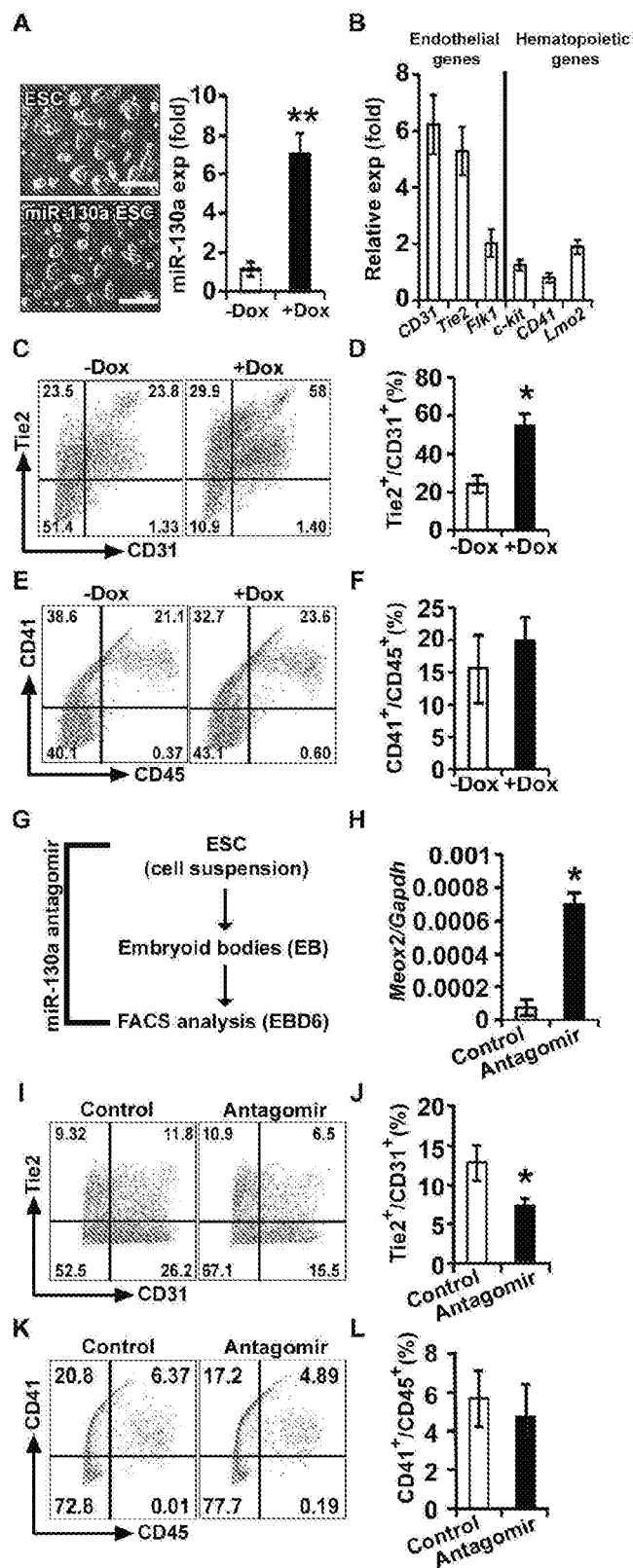
FIGS. 2A-L show miR-130a promotes the endothelial lineage. (A) Left panels: phase contrast images of wild-type E14 (ES cells) and Dox-inducible miR-130a ES cell (miR-130a iES) colonies. Right panel: qPCR analysis of miR-130a in the absence (−Dox) and presence of Dox (+Dox). (B) qPCR analyses for endothelial and hematopoietic markers using −Dox and +Dox EBs at d6 of differentiation (ratio shown as +Dox/−Dox). (C-F) FACS profiles (C, E) and quantification (D, F) of endothelial (Tie2 and CD31 (C, D)); and hematopoietic (CD41 and CD45 (E, F)) markers in −Dox and +Dox conditions. (G) Schematic representation of the miR-130a knockdown approach in the ES/EB system. (H) qPCR analysis of Meox2 using RNA isolated from control and miR-130a antagomir transfected cells. (I-L) FACS profiles (I, K) and quantification (J, L) of endothelial (Tie2 and CD31 (I, J)) and hematopoietic (CD41 and CD45 (K, L)) markers in control and antagomir-treated EBs. Error bars indicate SEM (n=4; *p<0.05). Scale bar: 200 μm (see also FIG. 6).
Figure 6:
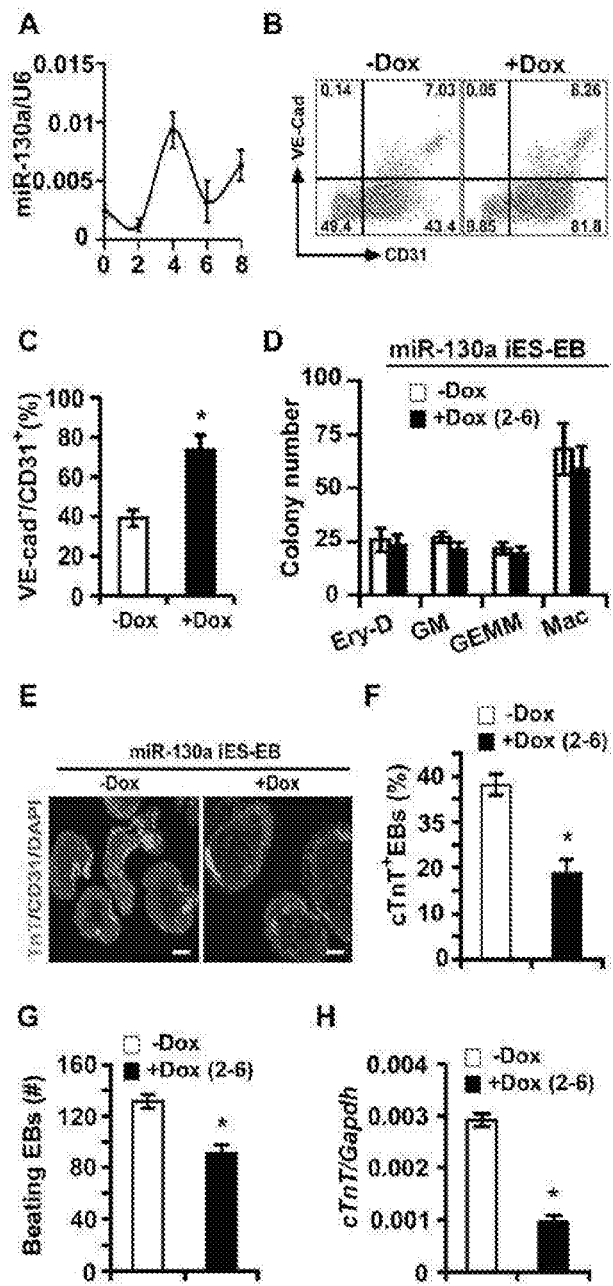
FIGS. 6A-H are related to FIG. 2; miR-130a induces the endothelial program and suppresses the cardiogenic program without impacting hematopoiesis. (A) qPCR analyses of mature miR-130a during ES/EB differentiation. (B, C) FACS profile (B) and quantification (C) of endothelial lineages (VE-Cadherin and CD31) markers in the presence of Dox (+Dox) as compared to no Dox (−Dox). (D) Hematopoietic colony forming cell (CFC) assays from induced (+Dox) and uninduced (−Dox) miR-130a iES/EBs. (E) Representative sections of −Dox and +Dox miR-130a iES/EBs immunostained with cTnT (green), CD31 (red) and counterstained with DAPI (blue) at d10 of EB differentiation. (F) Quantitative analysis of cTnT$^+$ EBs in 142 induced (+Dox) and 123 uninduced (−Dox) EBs. (G) Contractility assay from 130 induced (+Dox) and 136 uninduced (−Dox) EBs. (H) qPCR analyses of a cardiac marker (cTnT) from induced (+Dox) and uninduced (−Dox) miR-130a iES/EBs. Error bars indicate SEM (n=4; *p<0.05). Scale bar: 200 μm.

To identify a specific miRNA that regulates the hemato-endothelial lineages, Flk1$^+$ cells from d4 EBs were FACS sorted and a robust enrichment of miR-130a in Flk1$^+$ cells was observed relative to Flk1$^-$ cells (FIG. 5D). To evaluate the enriched expression of miR-130a in the endothelial lineages in vivo, CD31$^+$, CD41$^+$, and cardiac progenitor cells (CPCs) from E9.5 embryos were sorted and miR-130a expression analysis was performed. A robust expression of miR-130a in CD31$^+$ cells was detected relative to other lineages (FIG. 5E). These results indicated that miR-130a is enriched in the endothelial progenitors. FACS-sorted CD31$^+$ cells from the Etv2$^{Cre/+}$; Dicer$^{L/L}$ embryos demonstrated reduced expression of mature miR-130a, indicating that Dicer is required for miR-130a biogenesis in the Etv2$^+$ lineage (FIG. 1G). To define the regulatory network for miR-130a, the 5.0 kb upstream region of the miR-130a locus was analyzed and three highly conserved binding motifs for Etv2 (FIG. 1H) were identified. Doxycycline (Dox) inducible HA-Etv2 ES cell line (Koyano-Nakagawa et al., 2012) was utilized to examine the binding of Etv2 to the miR-130a promoter in vivo. ChIP assay using Dox-induced cell lysates showed a 15-fold enrichment of Etv2 at the cis-regulatory region of the miR-130a promoter, but not in the non-specific region of the miR-130a locus (FIG. 1I). Gel-shift assays further confirmed that Etv2 could bind to the miR-130a promoter containing the Etv2 recognition sequence (FIG. 1J). Transcriptional assays using the 1.0 kb miR-130a promoter-reporter construct revealed that Etv2 potently trans-activated the miR-130a promoter in a dose-dependent fashion. Mutagenesis of the Etv2 binding motifs resulted in abolishment of the transcriptional activity (FIG. 1K). To monitor whether Etv2 could regulate miR-130a expression in vivo, the Etv2-EYFP$^+$ cells from the Etv2-wildtype (Etv2$^{+/+}$) and null (Etv2$^{-/-}$) embryos at E7.5 were FACS sorted. qPCR analysis for miR-130a showed reduced expression of miR-130a in Etv2$^{-/-}$ embryos compared to controls (FIG. 1L). These results indicated that miR-130a was expressed in early endothelial progenitors and that Etv2 is a direct upstream regulator of miR-130a.

miR-130a Modulates the Endothelial Lineage During Embryogenesis qPCR analysis using ES/EBs revealed that mature miR-130a transcripts were induced by d4 (hemato-endothelial specification stage) and remained high at d8 (endothelial maturation stage) of EB differentiation (FIG. 6A). To define the role miR-130a in endothelial progenitors, inducible ESC line was generated which over-expresses miR-130a in response to Dox (miR-130a iES). Stable integration of the miR-130a construct did not alter colony morphology (FIG. 2A, left panel), and addition of Dox resulted in a significant increase (~7 fold) of the miR-130a transcript (FIG. 2A, right panel). Dox-mediated induction of miR-130a from d2-d6 resulted in increased expression of endothelial transcripts including: CD31, Tie2, and Flk1 with no effect in the key hematopoietic transcripts including CD41, c-kit and Lmo2 (FIG. 2B). Similar to the qPCR results, FACS analysis revealed that the over-expression of miR-130a resulted in an increase of the endothelial program (CD31$^+$/Tie2$^+$ and CD31$^+$/VE-cadherin populations) by 2.5-fold and 2-fold, respectively (FIGS. 2C and 2D; FIGS. 6B and 6C) without any significant changes in the hematopoietic lineage (CD41$^+$/CD45$^+$ population) at d6 of EB differentiation (FIGS. 2E and 2F). Colony forming (CFC) assays revealed that the definitive hematopoietic colonies (Ery-D, GEMM, GM and Mac) were not significantly changed between uninduced and Dox-induced ES/EBs (FIG. 6D). These data demonstrated that miR-130a promoted the endothelial lineage with no effect on hematopoiesis. To examine the differential effect of miR-130a, miR-130a antagomir-mediated knockdown assays were performed using ES/EBs (FIG. 2G). Knockdown of miR-130a resulted in a robust increase in Meox2 (a known target of miR-130a (Chen and Gorski, 2008)) expression (FIG. 2H). FACS analysis revealed that functional inhibition of miR-130a resulted in a significant reduction of the endothelial lineage (FIGS. 2I and 2J), whereas the hematopoietic lineages were unaffected (FIGS. 2K and 2L). These results confirmed the preferential effect of miR-130a on endothelial development.

To examine whether miR-130a induction affects other mesodermal-derived lineages, immunohistochemical analyses was performed for cardiac and endothelial markers in differentiating miR-130a iES/EBs. Dox-induction of miR-130a from d2-d6 resulted in a significant reduction of cardiac Troponin (cTnT) expression in d10 EBs with a corresponding increase of CD31 expression (FIG. 6E). Quantitative assessment of the number of cTnT$^+$ EBs and beating EBs following miR-130a overexpression revealed a significant decrease in the cardiogenic program compared to controls (−Dox) (FIGS. 6F and 6G). Furthermore, qPCR analysis revealed decreased expression of cTnT, concurrent with reduced cardiac contractility in the Dox-induced EBs (FIG. 6H). These data suggested that miR-130a promoted the endothelial lineage at the expense of the cardiac program.

miR-130a Targets Pdgfra Expression and Modulates Mesodermal Lineage Development

Figure 3:
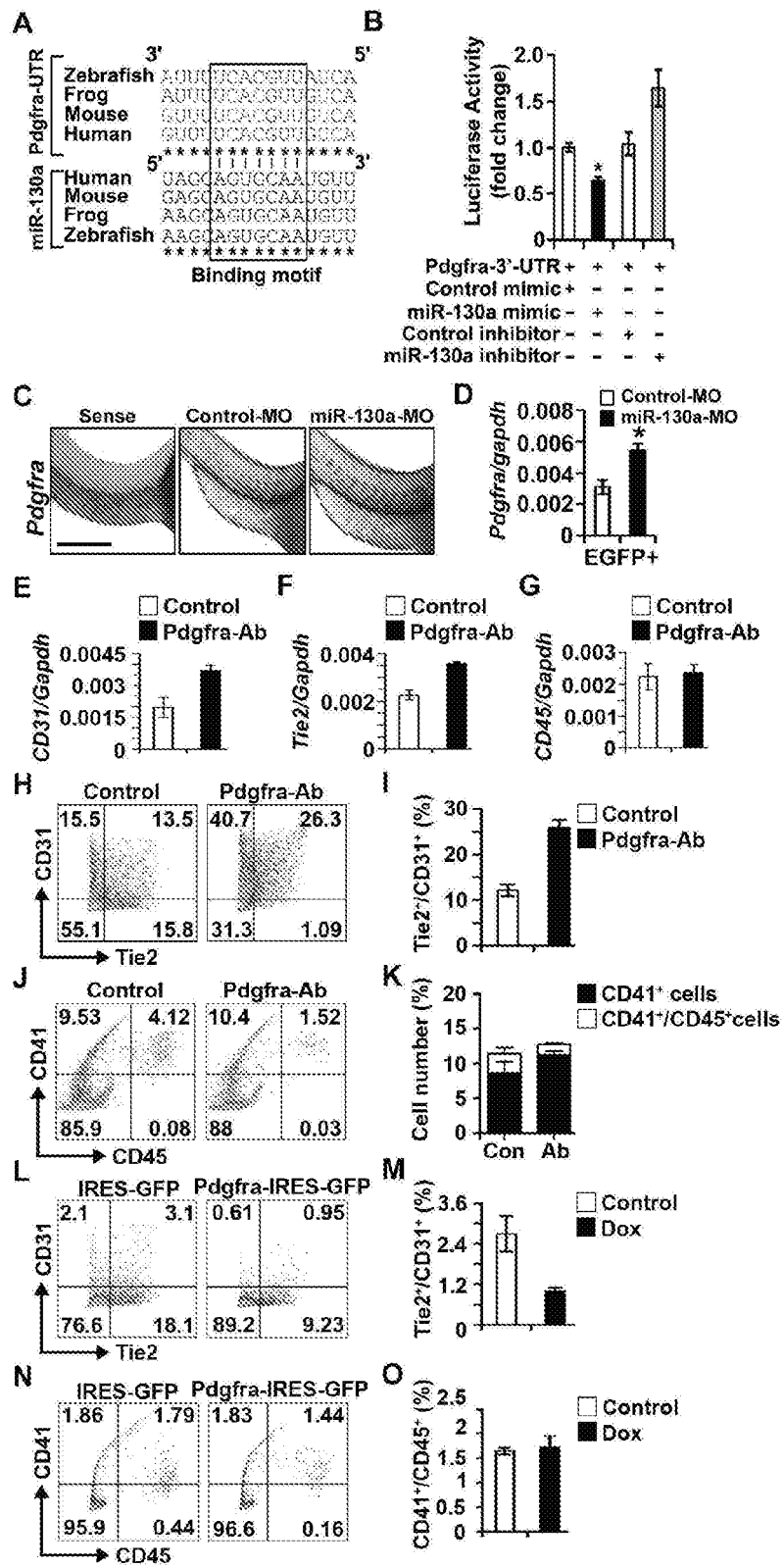
FIGS. 3A-O show miR-130a targets Pdgfra and miR-130a-Pdgfra pathway modulates mesodermal progenitors. (A) ClustalW multiple sequence alignment of Pdgfra 3' UTR and miR-130a. (B) Luciferase activity of Luc-Pdgfra-3'-UTR reporter constructs in the presence of miR-130a mimic and miR-130a inhibitor. (C) Whole-mount in situ hybridization images of control and miR-130a morphants using Pdgfra probes at 48 hpf. (D) qPCR analysis of Pdgfra transcripts using fli1-EYFP$^+$ sorted cells from control and miR-130a morphants at 48 hpf. (E-G) qPCR analysis of CD31, Tie2 and CD45 transcripts from control and Pdgfra neutralizing antibody-treated EBs at d6 of differentiation. (H-K) FACS profile (H, J) and quantification (I, K) of endothelial lineages (Tie2 and CD31 (H, I)) and hematopoietic lineages (CD41 and CD45 (J, K)) in control and Pdgfra neutralizing antibody-treated EBs at d6 of differentiation. (L-O) FACS profile (L N) and quantification (M, O) of endothelial lineages (Tie2 and CD31 (L, M)) and hematopoietic lineages (CD41 and CD45 (N, O)) using d6 EB in control and Pdgfra over-expression conditions. Error bars indicate SEM (n=4; *p<0.05). Scale bar: 200 μm.

To explore the mechanism by which miR-130a modulates endothelial lineage development, three miRNA target prediction tools including TargetScan 6.2, PicTar and miRANDA were employed to mine comnunon predicted targets. Among the multiple targets, Pdgfra was identified as a highly conserved target of miR-130a with a high percentile score using TargetScan 6.2 in both mouse and zebrafish genomes (data not shown). Multiple sequence alignment revealed a highly conserved miR-130a seed-sequence in the Pdgfra-3'-UTR region (FIG. 3A). To examine whether miR-130a targets Pdgfra mRNA, luciferase assays using a PGK promoter-driven luciferase reporter (PGK-Luc-Pdgfra-3'-UTR) construct were performed. Co-transfection of the PGK-Luc-Pdgfra-3'-UTR reporter with a miR-130a mimic resulted in a statistically significant reduction (~40%) of the luciferase activity, whereas, co-transfection with miR-130a inhibitor resulted in enhancement of the luciferase activity, indicating that endogenous miR-130a could target the Pdgfra mRNA (FIG. 3B). To assess whether miR-130a could target Pdgfra transcripts in vivo, mopholinos against miR-130a (miR-130a-MO) were injected at the one-two cell stage into fertilized zebrafish eggs and performed in situ hybridization for Pdgfra mRNA. The data demonstrated increased expression of Pdgfra in the miR-130a morphants, indicating that miR-130a could suppress Pdgfra expression in viro (FIG. 3C). To further examine its effect on the endothelial lineage, endothelial specific transgenic reporter [Tg(fli1-EGFP)] line was utilized and injected control MO or miR-130a MO into the fertilized eggs. qPCR analysis from FACS sorted fli1-EGFP+ cells revealed enrichment of Pdgfra transcripts in the miR-130a morphants relative to the control (FIG. 3D). These results indicated that miR-130a could target Pdgfra transcripts both in vitro and in vivo.

Figure 4:
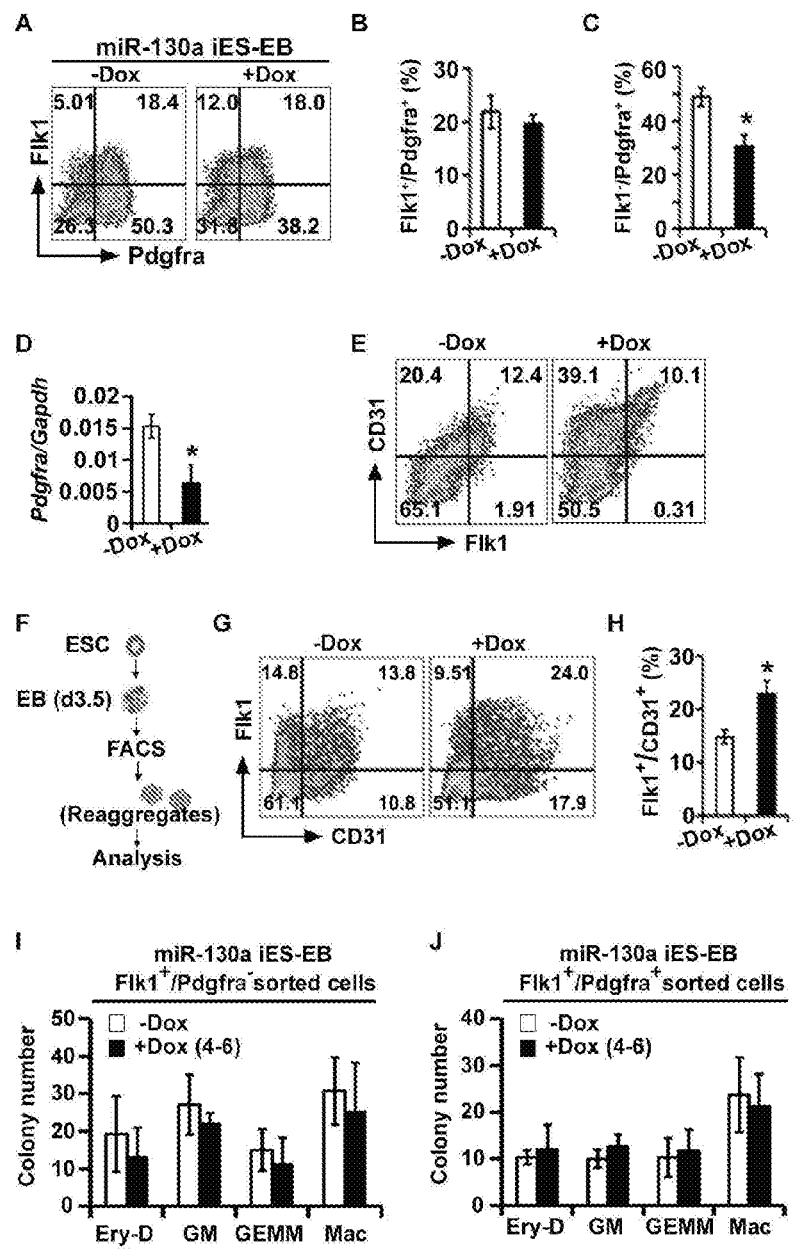
FIGS. 4A-J show miR-130a targets Pdgfra in vivo and promotes lateral plate mesodermal lineage. (A-C) FACS profile (A) and quantification (B, C) of mesodermal populations in miR-130a iES/EB differentiation in −Dox and +Dox conditions. (D) qPCR analysis of Pdgfra in −Dox and +Dox conditions using d4 EBs. (E) FACS profile of endothelial (Flk1 and CD31) markers during miR-130a iES/EB differentiation in −Dox and +Dox conditions. (F) Schematic of the experiment to determine the ability of miR-130a to re-specify mesoderm. (G, H) FACS profiles (G) and quantification (H) of endothelial (Flk1 and CD31) markers at d6. (I, J) Hematopoietic colony forming assay from Flk1$^+$/Pdgfra$^-$ (I) and Flk$^+$/Pdgfra$^+$ (J) sorted cells using d3.5 miR-130a iES/EB system. Error bars indicate SEM (n=3; *p<0.05). (see also FIG. 7).
Figure 7:
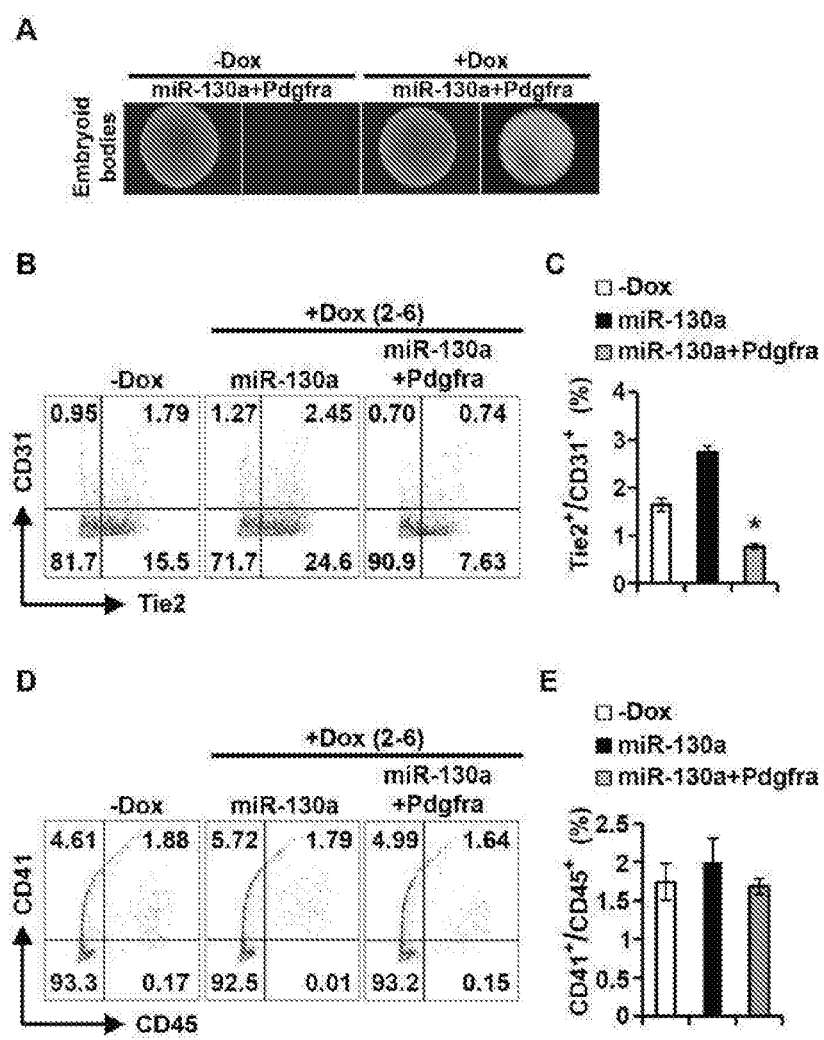
FIGS. 7A-E are related to FIG. 4; miR-130a modulates the endothelial program via Pdgfra signaling. (A) Images of differentiating EBs obtained from miR-130a+Pdgfra; IRES-GFP inducible ES cell lines in the absence (−Dox) and presence of Dox (+Dox). (B-E). FACS profiles (B, D) and quantification (C, E) of endothelial lineages (Tie2 and CD31 (B, C)) and hematopoietic lineages (CD41 and CD45 (D, E)) during d6 of miR-130a+Pdgfra iES/EB differentiation. Error bars indicate SEM (n=3; *p<0.05).

Next, it was examined whether down regulation of Pdgfra regulation is the mechanism by which miR-130a regulates endothelial lineages. Antibody-mediated inhibition of Pdgfra signaling resulted in a significant induction of CD31 and Tie2 transcripts, but had no effect on CD45 transcript levels (FIGS. 3E-G). Similarly, FACS analysis showed that blocking Pdgfra signaling led to a significant increase in the endothelial lineage (Tie2$^+$/CD31$^+$ cell population from 13.5%±2.0% to 26.1%±3.0%) with no effect on the hematopoietic lineage (FIGS. 3H-K). To validate these findings, a Dox-inducible lentiviral vector expressing Pdgfra was generated. In contrast to the inhibition studies, lentiviral-mediated Dox-inducible overexpression of Pdgfra repressed the endothelial program (Tie2$^+$/CD31$^+$ cell population decreased from 3.13%±0.25% to 0.95%±0.50%) without affecting the hematopoietic lineage (FIGS. 3L-O). These results demonstrated that modulation of Pdgfra signaling had a profound effect on the endothelial lineage, but not on the hematopoietic lineage during development.

miR-130a Modulates Flk1$^+$/Pdgfra$^+$ Mesodermal Progenitors Towards Lateral Plate Mesodermal Lineage Previous studies have shown that Flk1$^-$/Pdgfra$^+$ (paraxial mesoderm) and Flk1$^+$/Pdgfra$^-$ (lateral plate mesoderm) cells arise from the Flk1$^+$/Pdgfra$^+$ cell population by modulating Pdgfra levels at early stages of ES/EB differentiation (Kataoka et al., 2011: Sakurai et al., 2006). Therefore, a shorter pulse (48 h) was performed and it was examined whether miR-130a promoted the endothelial lineage from mesodermal progenitors by suppressing Pdgfra expression. A 48 h Dox pulse between d2-d4 using miR-130a iES/EBs resulted in a markedly reduced percentage (54%±4% to 35%±2%) of the Flk1$^-$/Pdgfra$^+$, but not Flk1$^+$/Pdgfra$^+$ populations (FIGS. 4A-C). Congruent with the luciferase activity and the FACS data, qPCR analyses showed reduced levels of Pdgfra transcripts in Dox-pulsed miR-130a EBs, indicating that miR-130a targets Pdgfra mRNA (FIG. 4D). Also observed was a small but non-significant increase in Flk1$^+$/Pdgfra$^-$ populations (data not shown). Notably, similar to a long pulse (d2-6) of miR-130a (FIG. 2), a shorter pulse (d2-4) resulted in an equivalent promotion of the endothelial lineage (FIG. 4E). To further investigate the correlation between miR-130a and Pdgfra signaling, an inducible Pdgfra mouse ES cell line was engineered using miR-130a iES cells, which over-expresses both miR-130a and Pdgfra in response to doxycycline (miR-130a$^+$Pdgfra iES) (FIG. 7A). As expected, induction of miR-130a alone resulted in an induction of the endothelial lineage. Forced overexpression of miR-130a and Pdgfra resulted in a significant reduction of Tie2$^+$/CD31$^+$ cells (2.45%±0.80% to 0.74%±0.20%) with no effect on the hematopoietic populations (FIGS. 7B-E). These data further supported the hypothesis that miR-130a regulates the endothelial lineage via down-regulation of Pdgfra signaling.

Aggregation-reaggregation assays were performed to test the ability of miR-130a to modulate mesodermal precursors. Uninduced FACS sorted Flk1$^+$/Pdgfra$^-$ and Flk1$^+$/Pdgfra$^+$ cells from miR-130a iES/EBs (d3.5) were reaggregated for an additional 48 h in the absence or presence of Dox and were analyzed for mesodermal-derivatives at d6 using cell surface markers (FIG. 4F). No significant differences were detected in the number of endothelial cells derived from the Flk1$^+$/Pdgfra$^-$ population, demonstrating that over-expression of miR-130a did not influence the fate of lineage-committed endothelial populations (data not shown). FACS analyses of Flk1$^+$/Pdgfra$^+$ reaggregates revealed an emergence of the endothelial lineages (FIG. 4G), supporting the existence of early unpatterned mesodermal cells within this population (Sakurai et al., 2006). A Dox-pulse (d4-6) in the double-positive reaggregates resulted in a significant increase (12%±3% to 22%±2%) of endothelial cells (FIGS. 4G and 4H). In contrast, the blood colony forming activity from either Flk1$^+$/Pdgfra$^-$ or Flk1$^+$/Pdgfra$^+$ cell populations did not show significant changes (FIGS. 4I and 4J), demonstrating that the effect of miR-130a is specific to the promotion of the endothelial lineage. These data indicated that miR-130a directed the mesodermal lineage towards lateral plate mesoderm by suppression of Pdgfra expression.

Discussion

Defined herein is the role of the Etv2-miR-130a-Pdgfra network in the divergence of hemato-endothelial progenitors. Mechanistically, miR-130a promotes endothelial lineage development by modulating Pdgfra signaling. This is the first report of a miRNA that specifically promotes the endothelial lineage without affecting the hematopoietic lineage.

miRNAs are regulators of transcript expression, however, only a limited number of miRNAs have specific developmental roles. For example, the miR-430/427/302 family controls mesendodermal fate specification and miR-1/miR- 133 (muscle-specific miRNAs) can promote mesodermal formation during embryogenesis (Ivey et al., 2008; Rosa et al., 2009). The data herein reports a novel functional role for miR-130a that specifically promotes differentiation of the endothelial lineage.

Previous reports suggest that Etv2 plays a major role for the progression of Flk1+/Pdgfra+ progenitors (primitive mesoderm) to the Flk1+/Pdgfra− (vascular mesoderm) state (Kataoka et al., 2011). Based on the data, it is believed that the Etv2-miR-130a cascade down-regulates Pdgfra expression and promotes the transition of Flk1+/Pdgfra+ to the Flk1+/Pdgfra−. It is further believed that miR-130a facilitates the segregation of bipotent progenitors towards the endothelial lineage without affecting the hematopoietic lineage. However, the involvement of functionally redundant miRNAs cannot be ruled out.

Figure 8:
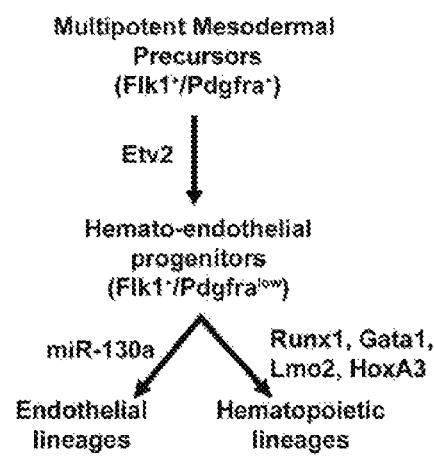
FIG. 8 depicts Etv2-miR-130a-Pdgfra network regulates endothelial development. A model summarizing the involvement of Etv2-miR-130a network in the regulation of hemato-endothelial development. Flk1 and Pdgfra are highly expressed in early multipotent mesodermal precursors (unpatterned mesoderm). Etv2 serves as a key mediator in the derivation of hemato-endothelial progenitors (Flk1$^+$/Pdgfralow) from mesodermal precursors by down-regulating Pdgfra. Among the Flk1$^+$/Pdgfralow hematoendothelial progenitor cells, those that express miR-130a will further down-regulate Pdgfra and have an endothelial fate. It is believed that this mechanism mediates the segregation of the endothelial lineage from the hemato-endothelial progenitors.
Figure 9:
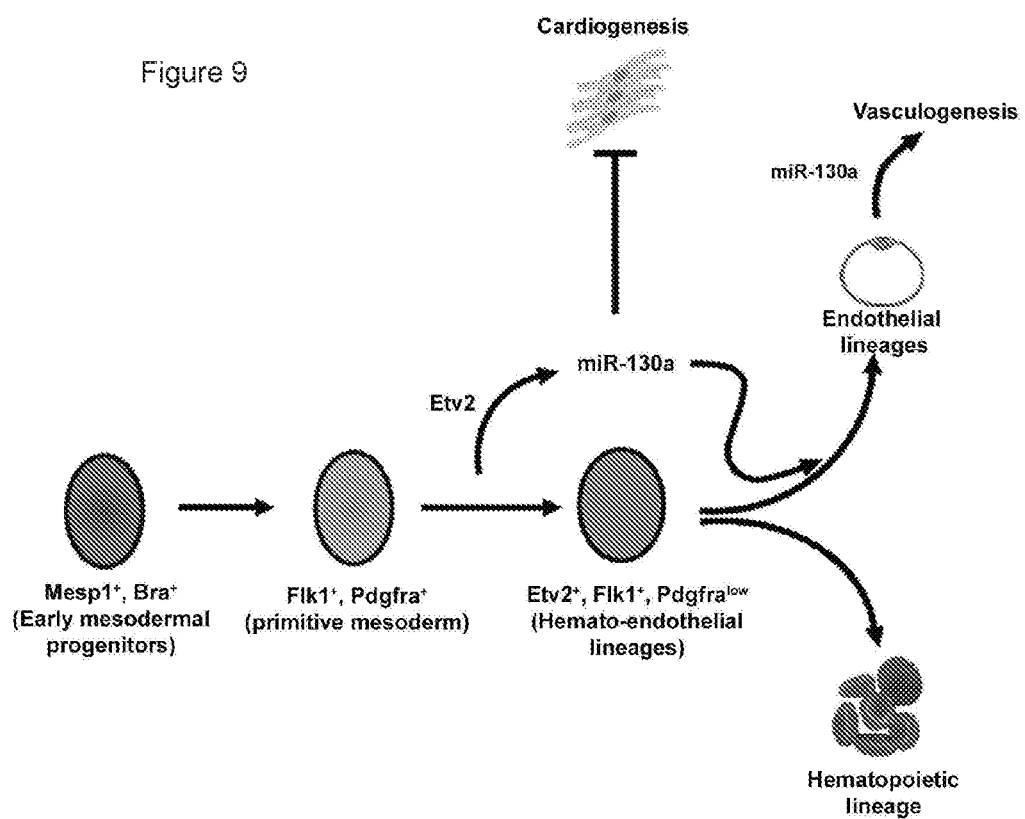
FIG. 9 provides a graphical presentation of the Etv2-miR-130a network.

Since mutation of Etv2 affects both hematopoietic and endothelial lineages (Koyano-Nakagawa et al., 2012), it was unexpected to discover that miR-130a targets Pdgfra and promotes only the endothelial lineage. However, these results are supported by the finding that fetal liver hematopoiesis was not affected in the Pdgfra conditional knockout embryos (Ding et al., 2013). The data herein together with others (Ding et al., 2013) support the notion that the endothelial, but not the hematopoietic lineage is sensitive to the level of Pdgfra. It is believed that as Flk1+/Pdgfra+ common mesodermal progenitors progress to the Flk1+/Pdgfra− hemato-endothelial progenitors, miR-130a further down-regulates Pdgfra expression to direct cells towards the endothelial lineage (FIG. 8). This is in agreement with a previous report highlighting that newly-generated Flk1 single positive cells are still plastic in nature and could switch between the Pdgfra single positive state (and vice versa) before lineage commitment (Sakurai et al., 2006). It is believed that the Etv2-miR-130a-Pdgfra pathway may function to stabilize this plastic intermediate state towards an endothelial fate by suppressing the fluctuating levels of Pdgfra. Early developmental events are regulated by multiple signaling pathways including FGF and Wnt signaling in a context-dependent manner. For example, inhibition of FGF-Erk1/2 signaling results in loss of Pdgfra+ cells (Kunath et al., 2007), whereas a Wnt signaling wave regulates cardiogenesis and hematopoiesis in a temporally distinct fashion (Naito et al., 2006). The data herein, together with others, illustrate the role of signaling pathways, transcription factors and miRNAs in the regulation of cell fate decisions, thereby forming an integral part of the regulatory network in the emergence of mesodermal lineages.

In summary, a novel role for miR-130a has been discovered in the modulation of early endothelial progenitors. While several factors including HoxA3, Runx1 and miR-142-3p have been shown to have a role in hematopoietic lineage segregation and hemangioblast specification (Iacovino et al., 2011; Nimmo et al., 2013), endothelial specific regulators have not been described. miR-130a is the first reported regulator of endothelial development from the hemato-endothelial progenitors (FIG. 8).

Example 2

*Mus musculus* ets variant 2 (Etv2) sequence information
NCBI Reference Sequence for mEtv2 gene: NM_007959.2
LOCUS:NM_007959 1050 bp mRNA linear ROD 15 Feb. 2015
DEFINITION:*Mus musculus* ets variant 2 (Etv2), mRNA.
ACCESSION:NM_007959 XM_909688
VERSION:NM_007959.2 GI:119964691
SOURCE:*Mus musculus* (house mouse)
Ensembi information for mEtv2 gene: Etv2 ENSMUSG0000006311
Description; ets variant 2 [Source:MGT Symbol; Acc:MGT:99253]
Location; Chromosome 7: 30,633,616-30,635,852 reverse strand.
INSDC coordinates;
chromosome:GRCm38:CM0001000.2:30633616:30635852:1
Name: Etv2 (MGI Symbol)
CCDS: This gene is a member of the Mouse CCDS set: CCDS39888.1
UniProtKB: Uniprot identifiers: P41163
RcfSeq: RcfSeq Gene ID 14008
mRNA sequence of mEtv2
gene="Etv2"
gene_synonym="Etsrp71"
standard_name="BE102623"
_xref="UniSTS:244290"

(SEQ ID NO: 14)

```
  1 agaaccgtca gaacaagcat ccatggacct gtggaactgg gatgaggcgt cactgcagga
 61 agtgcctcct ggggacaagc tgacaggact gggagcggaa tttggtttct atttccctga
121 agtggctcta caagaggaca caccgatcac accaatgaac gtagaaggct gctggaaagg
181 gttcccagag ctggactgga acccgctttt acctcacgaa gacgtaccett tccaggcgga
241 gcccgttgct caccccttc cgtggtcgcg agactggaca gacctgggat gcaacacctc
301 ggacccgtgg agctgtgctt cacagacgcc aggccctgcc cctcctggca cgagcccctc
361 cccctcgtc ggctttgaag gggcgaccgg ccagaatcct gccacctcgg caggaggggt
421 ccctcgtgg tcgcacccctc cagctgcctg gagcactacc agctgggact gttctgtggg
481 ccccagtggc gccacctact gggacaatgg cctgggcggg gaagcgcatg aggactataa
541 aatgtcatgg ggcgggtctg ccggttcgga ctacaccacc acgtggaata ctgggctgca
601 ggactgcagc atcccctttcg aggggcacca gagtccagca ttcaccacgc cctccaaatc
661 gaacaagcag tctgatagag ccacattgac tcgctactcc aaaactaacc accgaggtcc
721 cattcagctg tggcaattcc tcctggagct gctccacgac ggggctcgca gcagctgcat
```

-continued

```
 781 ccgctggacg ggcaatagcc gcgagttcca gctgtgcgac cccaaagagg tggcccggct 841 gtggggcgag cgcaagagga agccgggaat gaattatgag aaactgagtc gaggtctacg 901 ttattattac cgccgcgaca tcgtgctcaa gagtggtggg cgcaagtaca cataccgctt 961 cggggacgt gtgcctgtcc tcgcctatca ggatgatatg gggcatctgc caggtgcaga 1021 aggccaataa aacaaaaaac aaaaacaaaa
```

Protein Sequence of Mouse Etv2

(SEQ ID NO: 15)
MDLWNWDEASLQEVPPGDKLTGLGAEFGFYFPEVALQEDTPITPMNVEGC

WKGFPELDWNPALPHEDVPFQAEPVAHPLPWSRDWTDLGCNTSDPWSCAS

QTPGPAPPGTSPSPFVGFEGATGQNPATSAGGVPSWSHPPAAWSTTSWDC

SVGPSGATYWDNGLGGEAHEDYKMSWGGSAGSDYTTTWNTGLQDCSIPFE

GHQSPAFTTPSKSNKQSDRATLTRYSKTNHRGPIQLWQFLLELLHDGARS

SCIRWTGNSREFQLCDPKEVARLWGERKRKPGMNYEKLSRGLRYYYRRDI

VLKSGGRKYTYRFGGRVPVLAYQDDMGHLPGAEGQ

Human ets variant 2 (Etv2) sequence information
NCBI information from Gene ID 2116
Official symbol: ETV2
Official Full Name: ets variant 2
Primary source: HGNC:HGNC:3491
See related; Ensembl:ENSi00000105672; HPRD: 16871; MIM:609358;
Vega:OTTHUMG00000150545
Organism; Homo sapiens
Also known as; ER71; ETSRP71
Ensembl information for human Etv2 Gene: ETV2 ENSCG00000105672
Description: ets variant 2 [Source:HGNC Symbol; Acc: HGNC:3491]
Synonym: ER71
Location: Chromosome 19: 35,641,745-35,644,871 forward strand.
INSDC coordinates: chromosome:GRCh38:CM000681.2: 35641745:35644871:1
About this gene: This gene has 8 transcripts (splice variants), 30 orthologues, 12 paralogues, is a member of 2 Ensembl protein families and is associated with 23 phenotypes.
mRNA sequence of human ets variant 2 (ETV2), transcript variant 1
LOCUS: NM_014209 1510 bp
DEFINITION: Homo sapiens ets variant 2 (ETV2), transcript variant 1, mRNA.
ACCESSION: NM_014209 XM_290831
VERSION: NM_014209.3 GI:665821253

(SEQ ID NO: 16)
```
    1 ttcctgttgc agataagccc agcttagccc agctgacccc agacctctc ccctcactcc 61 ccccatgtcg caggatcgag accctgaggc agacagcccg ttcaccaagc ccccgcccc 121 gccccatca cccgtaaac ttctcccagc ctccgccctg ccctcaccca gcccgctgtt 181 ccccaagcct cgctccaagc ccacgccacc cctgcagcag ggcagcccca gaggccagca 241 cctatccccg aggctggggt cgaggctcgg ccccgcccct gcctctgcaa cttgagcctg 301 gctgcgaccc ctgctctgac gtctcggaaa attcccctt gcccaggccc ttggggagg 361 gggtgcatgg tatgaaatgg ggctgagacc cccggctggg ggcagaggaa cccgccagag 421 aacattcaga aggccttcat cgcatccatg gacctgtgga actgggatga ggcatcccca 481 caggaagtgc ctccaggaa caagctggca gggcttgaag gagccaaatt aggcttctgt 541 ttccctgatc tggcactcca aggggacacg ccgacagcga cagcagagac atgctggaaa 601 ggtacaagct catccctggc aagcttccca cagctggact ggggctccgc gttactgcac 661 ccagaagttc catggggggc ggagcccgac tctcaggctc ttccgtggtc cggggactgg 721 acagacatgg cgtgcacagc ctgggactct tggagcgcg cctcgcagac cctgggcccc 781 gccctctcg gcccgggccc catccccgcc gccggctccg aaggcgccgc gggccagaac 841 tgcgtccccg tggcgggaga ggccacctcg tggtcgcgcg cccaggccgc cgggagcaac 901 accagctggg actgttctgt ggggcccgac ggcgatacct actggggcag tggcctgggc 961 ggggagccgc gcacggactg taccatttcg tggggcgggc ccgcgggccc ggactgtacc 1021 acctcctgga acccggggct gcatgcgggt ggcaccacct ctttgaagcg gtaccagagc 1081 tcagctctca ccgtttgctc cgaaccgagc ccgcagtcgg accgtgccag tttggctcga
```

```
1141 tgccccaaaa ctaaccaccg aggtcccatt cagctgtggc agttcctcct ggagctgctc 1201 cacgacgggg cgcgtagcag ctgcatccgt tggactggca acagccgcga gttccagctg 1261 tgcgacccca aagaggtggc tcggctgtgg ggcgagcgca agagaaagcc gggcatgaat 1321 tacgagaagc tgagccgggg ccttcgctac tactatcgcc gcgacatcgt gcgcaagagc 1381 gggggggcgaa agtacacgta ccgcttcggg ggccgcgtgc ccagcctagc ctatccggac 1441 tgtgcgggag gcggacgggg agcagagaca caataaaaat tcccggtcaa acctcaaaaa 1501 aaaaaaaaaa
```

Protein sequence of human ets variant 2 (ETV2), transcript variant 1
product="ETS translocation variant 2 isoform 1"
protein_id="NP_055024.2"
db_xref="GT:153791178"
db_xref="CCDS:CCDS32995.2"
db_xref="GeneID:2116"
db_xref="HGNC:HGNC:3491"
db_xref="MIM:609358"

(SEQ ID NO: 17)
MDLWNWDEASPQEVPPGNKLAGLEGAKLGFCFPDLALQGDTPTATAETCW

KGTSSSLASFPQLDWGSALLHPEVPWGAEPDSQALPWSGDWTDMACTAWD

SWSGASQTLGPAPLGPGPIPAAGSEGAAGQNCVPVAGEATSWSRAQAAGS

NTSWDCSVGPGDGTYWGSGLGGEPRTDCTISWGGPAGPDCITTSWNPGLH

AGGTTSLKRYQSSALTVCSEPSPQSDRASLARCPKTNHRGPIQLWQFLLE

LLHDGARSSCIRWTGNSREFQLCDPKEVARLWGERKRKPGMNYEKLSRGL

RYYYRRDIVRKSGGRKYTYRFGGRVPSLAYPDCAGGGRGAETQ

Bibliography

Bernstein. E., et al. (2003). Nat. Genet. 35, 215-217.
Chen, Y., and Gorski, D. H. (2008). Blood 111, 1217-1226.
De Val, S., et al. (2008). Cell 135, 1053-1064.
Ding, G., et al. (2013). Dev. Dyn. 242, 254-268.
Ferdous, A., et al. (2009). Proc. Natl. Acad. Sci. USA 106, 814-819.
Harfe, B. D., et al. (2005). Proc. Natl. Acad. Sci. USA 102, 10898-10903.
Huber, T, L., et al. (2004) Nature 432, 625-630.
Iacovino, M., et al. (2011). Nat. Cell Biol. 13, 72-78.
Ivey, K. N., and Srivastava, D. (2010). Cell Stem Cell 7, 36-41.
Ivey, K. N., et al. (2008). Cell Stem Cell 2, 219-229.
Kataoka, H., et al. (2011) Blood 118, 6975-6986.
Kattman, S. J., et al. (2006). Dev. Cell 11, 723-732.
Koyano-Nakagawa, N., et al. (2012). Stem Cells 30, 1611-1623.
Kunath, T., et al. (2007) Development 134, 2895-2902.
Loebel, D. A., et al. (2003) Dev. Biol. 264, 1-14.
Naito, A. T., et al. (2006) Proc. Natl. Acad. Sci. USA 103, 19812-19817.
Nimmo, R., et al. (2013) Dev. Cell 26, 237-249.
Rasmussen. T. L., et al. (2011) Development 138, 4801-4812.
Rosa, A, et al. (2009) Dev. Cell 16, 517-527.
Shalaby, F., et al. (1995) Nature 376, 62-66.
Saga, Y., et al. (1999) Development 126, 3437-3447.
Sakurai, H., et al. (2006). Stem Cells 24, 575-586.
Ueno, H. and Weissman, I. L. (2006) Dev. Cell 11, 519-533.
Yang, W. J., et al. (2005). J. Biol. Chem. 280, 9330-9335.
Akiyama, R., et al. (2014). Development 141, 1104-1109.
Drukker, M., et al. (2012). Nat. Biotech. 30, 531-542.
Kouskoff, V., et al. (2005). Proc. Nat. Acad. Sci. USA 102, 13170-13175.
Motoike, T., et al. (2003). Genesis 35, 153-159.
Ng, J. K., et al. (2002). Development 129, 5161-5170.
Zhang, K., et al. (2014) J. Am. Coll. Cardiol. 63, 358-368.

All publications, patents, and patent applications mentioned in this specification are herein incorporated by reference to the same extent as if each individual publication, patent, or patent application was specifically and individually indicated to be incorporated by reference. In the event that the definition of a term incorporated by reference conflicts with a term defined herein, this specification shall control.

What is claimed is:

1. A method to differentiate cells comprising over-expressing miR-130a in Flk1+/Pdgfra$^{low}$ hemato-endothelial progenitors or Flk1+/Pdgfra+ mesodermal precursor cells, or nucleic acid having at least 95% identity miR-130a, so as to yield cells of endothelial lineage, wherein the nucleic acid is RNA.

2. The method of claim 1, wherein the cells are mammalian cells.

3. The method of claim 1, further comprising admixing the endothelial lineage cells with a pharmaceutically acceptable carrier or a cell culture medium.

4. The method of claim 1, wherein cells administered to the subject are autologous or allogeneic.

5. A composition comprising $Flk1^+/Pdgfra^{low}$ hemato-endothelial progenitors or $Fkl1^+/Pdgfra^+$ mesodermal precursor cells overexpressing mir-130a and a carrier.

6. The composition of claim 5, wherein the cells are mammalian.

* * * * *

UNITED STATES PATENT AND TRADEMARK OFFICE
CERTIFICATE OF CORRECTION

PATENT NO. : 10,858,627 B2
APPLICATION NO. : 15/748772
DATED : December 8, 2020
INVENTOR(S) : Garry et al.

It is certified that error appears in the above-identified patent and that said Letters Patent is hereby corrected as shown below:

On the Title Page

Item [72], delete "Koyano-Nakagawa," and insert --Koyano,-- therefor

Column 2, item [56], under "Other Publications", Line 4, delete "Etv2/mir-130a/pdgfra" and insert --Etv2/miR-130a/pdgfra-- therefor In the Specification Column 1, Line 9, delete "201_7/020009" and insert --2017/020009-- therefor Column 4, Lines 52-53, delete "(Flk1+/Pdgfralow)" and insert --(Flk1$^+$/Pdgfra$^{low}$)-- therefor Column 4, Line 54, delete "Flk1+/Pdgfralow" and insert --Flk1$^+$/Pdgfra$^{low}$-- therefor Column 4, Line 54, delete "hematoendothelial" and insert --hemato-endothelial-- therefor Column 16, Line 64, delete "EYFP+" and insert --EYFP$^+$-- therefor Column 17, Line 39, delete "0.2 g/well" and insert --0.2 µg/well-- therefor Column 19, Line 43, delete "Flk1-/Pdgfra+" and insert --Flk1$^-$/Pdgfra$^+$-- therefor Column 21, Line 14, delete "comnunon" and insert --common-- therefor Column 21, Line 40, delete "flil-EGFP+" and insert --flil-EGFP$^+$-- therefor In the Claims Column 39, Lines 65-66, in Claim 1, delete "to differentiate cells comprising over-ex-pressing Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,858,627 B2 miR-130a in Flkl+/Pdgfra$^{low}$" and insert --of differentiating Flk1$^+$/Pdgfra$^-$-- therefor Column 39, Line 67, Claim 1, delete "Fkl1$^+$/Pdgfra$^+$" and insert --Flk1$^+$/Pdgfra$^+$-- therefor Column 39, Line 67, Claim 1, delete "cells, or" and insert --cells into cells of endothelial lineage comprising,-- therefor Column 40, Lines 63-65, Claim 1, delete "nucleic acid having at least 95% identity miR-130a, so as to yield cells of endothelial lineage, wherein the nucleic acid is RNA." insert a linebreak and --introducing a nucleic acid encoding miR-130a or a RNA having at least 95% identity to miR-130a in said Flk$^+$/Pdgfra$^-$ hemato-endothelial progenitors or Flk1$^+$/Pdgfra$^+$ mesodermal precursor cells to overexpress said miR-130a or RNA having at least 95% identity to miR-130a, wherein the overexpression of said miR-130a or RNA having at least 95% identity to miR-130a results in differentiation of said Flk1$^+$/Pdgfra$^-$ hemato-endothelial progenitors or Flk1$^+$/Pdgfra$^+$ mesodermal precursor cells into cells of endothelial lineage; and
administering said cells of endothelial lineage to a subject in need thereof so as to treat a cardiovascular disease, wound healing, and/or repopulation of vasculature.-- therefor Column 41, Line 6, Claim 5, delete "Flk1$^+$/Pdgfra$^{low}$" and insert --Fik1$^+$/Pdgfra$^-$-- therefor Column 41, Line 8, Claim 5, delete "mir-130a" and insert --miR-130a, wherein said Flk1$^+$/Pdgfra$^-$ hemato-endothelial progenitors or Flk1$^+$/Pdgfra$^+$ mesodermal precursor cells are genetically altered to comprise a nucleic acid encoding miR-130a to overexpress miR-130a,-- therefor